(12) United States Patent
Pasternak et al.

(10) Patent No.: US 9,926,317 B2
(45) Date of Patent: *Mar. 27, 2018

(54) INHIBITORS OF THE RENAL OUTER MEDULLARY POTASSIUM CHANNEL

(71) Applicant: Merck Sharp & Dohme Corp., Rahway, NJ (US)

(72) Inventors: Alexander Pasternak, Princeton, NJ (US); Ian Davies, Princeton, NJ (US); Fa-Xiang Ding, Staten Island, NY (US); Jinglong Jiang, Scotch Plains, NJ (US); Shuzhi Dong, Plainsboro, NJ (US); Xin Gu, Scotch Plains, NJ (US)

(73) Assignee: Merck Sharp Dohme Corp., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/323,985

(22) PCT Filed: Jul. 9, 2015

(86) PCT No.: PCT/US2015/039634
§ 371 (c)(1),
(2) Date: Jan. 5, 2017

(87) PCT Pub. No.: WO2016/010801
PCT Pub. Date: Jan. 21, 2016

(65) Prior Publication Data
US 2017/0197964 A1 Jul. 13, 2017

Related U.S. Application Data

(60) Provisional application No. 62/023,981, filed on Jul. 14, 2014.

(51) Int. Cl.
*C07D 471/10* (2006.01)
*A61K 31/438* (2006.01)
*A61K 31/444* (2006.01)
*A61K 45/06* (2006.01)

(52) U.S. Cl.
CPC .......... *C07D 471/10* (2013.01); *A61K 31/438* (2013.01); *A61K 31/444* (2013.01); *A61K 45/06* (2013.01)

(58) Field of Classification Search
CPC ............................ C07D 471/10; A61K 31/438
USPC ......................................................... 546/15
See application file for complete search history.

(56) References Cited

U.S. PATENT DOCUMENTS

| 2007/0275990 A1 | 11/2007 | Ohmoto et al. | |
| 2011/0224231 A1 | 9/2011 | Brodney et al. | |
| 2014/0031349 A1 | 1/2014 | Ding et al. | |
| 2016/0024091 A1* | 1/2016 | Pasternak | A61K 31/675 |
| | | | 514/91 |

FOREIGN PATENT DOCUMENTS

| WO | 2013062900 A1 | 5/2013 |
| WO | 2014150132 | * 9/2014 |
| WO | WO2016008064 A1 | 1/2016 |
| WO | WO2016010801 A1 | 1/2016 |
| WO | WO2016010802 A1 | 1/2016 |

OTHER PUBLICATIONS

Bhave,G., Development of a selective small-molecule inhibitor Kir1.1, the renal outer medullary potassium channel, Mol. Pharmacol., 2011, 42-50, 79.
Hebert, S. C. et al., Molecular Diversity and Regulation of Renal Potassium Channels, Physiol Rev., 2005, p. 319-371, vol. 85.
Ho, K. et al., Cloning and expression of an inwardly rectifying ATP-regulated potassium channel, Nature, 1993, p. 31-38, vol. 362.
Ji. W. et al., Rare independent mutations in renal salt handling genes contribute to blood pressure variation, Nature Genetics, 2008, p. 592-599, vol. 40, No. 5.
Lewis, L. M., High-throughput screening reveals a small-molecule inhibitor of the Renal Outer Medullary Potassium Channel and Kir7.1, Mol. Pharncol., 2009, 1094-1103, 76.
Lifton, R. P. et al., Molecular Mechanisms of Human Hypertension, Cell, 2001, p. 545-556, vol. 104.
Lorenz, J. N. et al., Impaired Renal NaCl Absorption inMic Lacking the ROMK Potassium Cannel, a Model for Type II Bartter's Syndrome, The Journal of Biological Chemistry, 2002, p. 37871-37830, vol. 277, No. 40.
Lu, M. et al., Absence of Small Conductance K+ Channel (SK) Activity in Apical Membranes of Thick Ascending Limb and Cortical Collectiong Duct in ROMK (Bartter's) Knockout Mice, The Journal of Biological Chemistry, 2002, p. 37881-37887, vol. 277, No. 40.
Nomura, Y. et al., Synthesis and Structure-Activity Relationships of 2-(4-Benzhydryl-1-piperazinyl)-1-phenylethanols as New Calcium Blockers, Chem. Phar. Bull, 1995, p. 241-246, vol. 43, No. 2.

(Continued)

*Primary Examiner* — Niloofar Rahmani
(74) *Attorney, Agent, or Firm* — Sarah Hooson; Catherine D. Fitch

(57) ABSTRACT

The present invention provides compounds of Formula I and the pharmaceutically acceptable salts thereof, which are inhibitors of the ROMK (Kir1.1) channel. The compounds may be used as diuretic and/or natriuretic agents and for the therapy and prophylaxis of medical conditions including cardiovascular diseases such as hypertension, heart failure and chronic kidney disease and conditions associated with excessive salt and water retention.

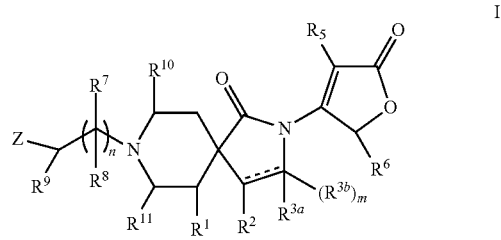

11 Claims, No Drawings

(56) References Cited

OTHER PUBLICATIONS

Reinalter, S. C. et al., Pharmacotyping of hypokalaemic salt-losing tubular disorders, Acta Physiol Scand, 2004, p. 513-521, vol. 181.

Shuck, M. E. et al., Cloning and Characterization of Multiple Forms of the Human Kidney ROM-K. Potassium Channel, The Journal of Biological Chemistry, 1994, p. 24261-24270, Vo. 269, No. 39.

Tobin, M. D. et al., Common Variants in Genes Underlying Monogenic Hypertension and Hypotension and Blood Pressure in the General Population; Hypertension, 2008, p. 1658-1664, vol. 51. No. 6.

Wang, W. et al., Renal potassium channesl: recent developments, Current Opinion in Nephrology and Hypertension, 2004, p. 549-555, vol. 13, No. 5.

Deng, Guanghui et al., Novel complex crystal structure of prolyl hydroxylase domain-containing protein 2 (PHD2):2,8-Diazaspiro;4.5]decan-1-ones as potent, orally bioavailable PHD2 inhibitors, Bioooganic & Medicinal Chemistry Letters, 2013, 6349-6358, 21.

Fritch et al., Design, syntheses, and SAR of 2,8-diazaspiro[4.5]decanones at T-type calcium channel antagonists, Bioorganic & Medicinal Chemistry Letters, 2010, 6375-6378, 20.

International Search Report for PCT/US2015/039634 dated Oct. 6, 2015, pp. 8.

\* cited by examiner

INHIBITORS OF THE RENAL OUTER MEDULLARY POTASSIUM CHANNEL

CROSS-REFERENCE TO RELATED APPLICATIONS

This application is a U.S. National Phase application under 35 U.S.C. § 371 of PCT Application No. PCT/US15/039634, filed on Jul. 9, 2015, which claims priority from and the benefit of U.S. Patent Application Ser. No. 62/023,981, filed Jul. 14, 2014.

FIELD OF THE INVENTION

The present invention relates to novel spirocyclic compounds and salts thereof useful as renal outer medullary potassium channel inhibitors. The present invention further relates to compositions containing such compounds, and methods of use thereof.

BACKGROUND OF THE INVENTION

The Renal Outer Medullary Potassium (ROMK) channel (Kir1.1) (see e.g., Ho, K., et al., *Cloning and expression of an inwardly rectifying ATP-regulated potassium channel*, Nature, 1993, 362(6415): p. 31-8.1, 2; and Shuck, M. E., et al., *Cloning and characterization of multiple forms of the human kidney ROM-K potassium channel*, J Biol Chem, 1994, 269(39): p. 24261-70) is a member of the inward rectifier family of potassium channels expressed in two regions of the kidney: thick ascending loop of Henle (TALH) and cortical collecting duct (CCD) (see Hebert, S. C., et al., *Molecular diversity and regulation of renal potassium channels*, Physiol Rev, 2005, 85(1): p. 319-713). At the TALH, ROMK participates in potassium recycling across the luminal membrane which is critical for the function of the $Na^+/K^+/2Cl^-$ co-transporter, the rate-determining step for salt reuptake in this part of the nephron. At the CCD, ROMK provides a pathway for potassium secretion that is tightly coupled to sodium uptake through the amiloride-sensitive sodium channel (see Reinalter, S. C., et al., *Pharmacotyping of hypokalaemic salt-losing tubular disorders*, Acta Physiol Scand, 2004, 181(4): p. 513-21; and Wang, W., *Renal potassium channels: recent developments*, Curr Opin Nephrol Hypertens, 2004, 13(5): p. 549-55). Selective inhibitors of the ROMK channel (also referred to herein as inhibitors of ROMK or ROMK inhibitors) are expected to represent novel diuretics for the treatment of hypertension and other conditions where treatment with a diuretic would be beneficial with potentially reduced liabilities (i.e., hypo- or hyperkalemia, new onset of diabetes, dyslipidemia) over the currently used clinical agents (see Lifton, R. P., A. G. Gharavi, and D. S. Geller, *Molecular mechanisms of human hypertension*, Cell, 2001, 104(4): p. 545-56). Human genetics (Ji, W., et al., *Rare independent mutations in renal salt handling genes contribute to blood pressure variation*, Nat Genet, 2008, 40(5): p. 592-9; and Tobin, M. D., et al., *Common variants in genes underlying monogenic hypertension and hypotension and blood pressure in the general population*, Hypertension, 2008, 51(6): p. 1658-64) and genetic ablation of ROMK in rodents (see Lorenz, J. N., et al., *Impaired renal NaCl absorption in mice lacking the ROMK potassium channel, a model for type II Bartter's syndrome*, J Biol Chem, 2002, 277(40): p. 37871-80 and Lu, M., et al., *Absence of small conductance K+ channel (SK) activity in apical membranes of thick ascending limb and cortical collecting duct in ROMK (Bartter's) knockout mice*, J Biol Chem, 2002, 277(40): p. 37881-7) support these expectations. To our knowledge, the first publicly disclosed small molecule selective inhibitors of ROMK, including VU590, were reported from work done at Vanderbilt University as described in Lewis, L. M., et al., *High-Throughput Screening Reveals a Small-Molecule Inhibitor of the Renal Outer Medullary Potassium Channel and Kir7.1*, Mol Pharmacol, 2009, 76(5): p. 1094-1103. The compound VU591 was later reported in Bhave, G. et al., *Development of a Selective Small-Molecule Inhibitor of Kir1.1, the Renal Outer Medullary Potassium Channel*, Mol Pharmacol, 2011, 79(1), p. 42-50, the text of which states that "ROMK (Kir1.1), is a putative drug target for a novel class of loop diuretics that would lower blood pressure without causing hypokalemia."

Since then, numerous ROMK inhibitors have been described.

The continued discovery of selective small molecule inhibitors of ROMK is needed for the development of new treatments for hypertension, heart failure, edematous states and related disorders. The compounds of Formula I and salts thereof of this invention are selective inhibitors of the ROMK channel and could be used for the treatment of hypertension, heart failure and other conditions where treatment with a diuretic or natriuretic would be beneficial.

SUMMARY OF THE INVENTION

The present invention provides compounds of Formula I

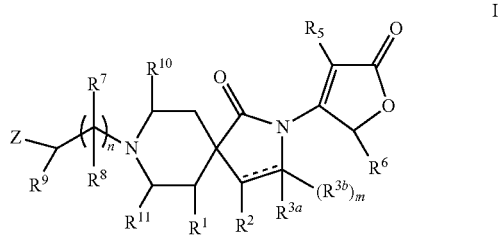

and the pharmaceutically acceptable salts thereof. The compounds of Formula I are inhibitors of the ROMK (Kir1.1) channel. As a result, the compounds of Formula I could be used in methods of treatment, inhibition or amelioration of one or more disease states that could benefit from inhibition of ROMK. The compounds of this invention could be used in methods of treatment which comprise administering a therapeutically or prophylactically effective amount of a compound of Formula I to a patient in need of a diuretic and/or natriuretic agent. Therefore, the compounds of Formula I could be valuable pharmaceutically active compounds for the therapy, prophylaxis or both of medical conditions, including, but not limited to, cardiovascular diseases such as hypertension and heart failure as well as chronic kidney disease, and conditions associated with excessive salt and water retention. The compounds of this invention could further be used in combination with other therapeutically effective agents, including but not limited to, other drugs which are useful for the treatment of hypertension, heart failure and conditions associated with excessive salt and water retention. The invention furthermore relates to processes for preparing compounds of Formula I, and pharmaceutical compositions which comprise compounds of Formula I. These and other aspects of the invention will be evident from the description contained herein.

DETAILED DESCRIPTION OF THE INVENTION

The present invention addresses the following compounds, compounds of (1)-(33):

(1) A compound of formula I:

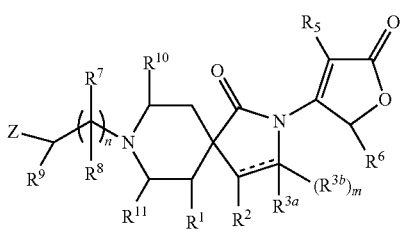

or a pharmaceutically acceptable salt thereof wherein:

Z is

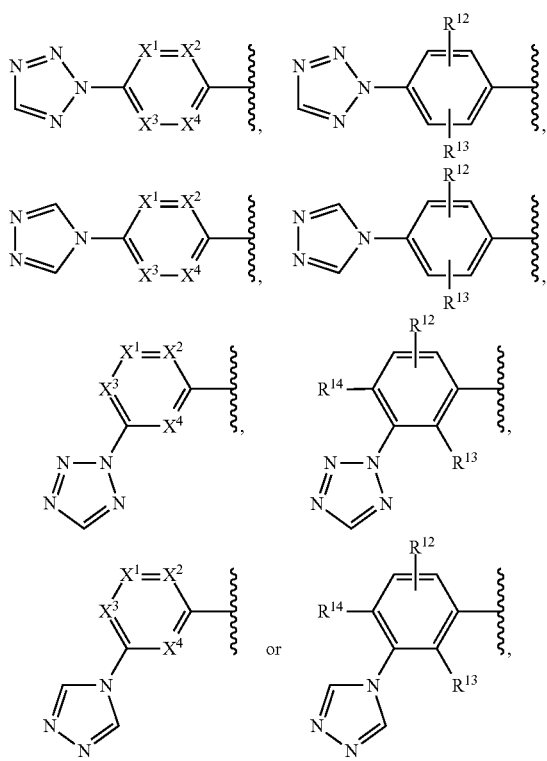

$X^1$, $X^2$, $X^3$ and $X^4$, where present, are each independently selected from $C(R^4)$ and N, provided that at least one and at most two of $X^1$, $X^2$, $X^3$ and $X^4$ are N;

$R^1$ is —H, halo, —OH, or —$OC_{1-3}$alkyl;

$R^2$ is —H, =O (oxo), —OH, —$C_{1-3}$alkyl or —$OC_{1-3}$alkyl;

$R^{3a}$ is —H, —$C_{3-4}$cycloalkyl or —$C_{1-3}$alkyl optionally substituted with —$OCH_3$ or 1 to 3 of —F;

$R^{3b}$ is —H or —$C_{1-3}$alkyl, or $R^{3b}$ is absent when the dashed bond is a double bond;

or $R^{3a}$ and $R^{3b}$ are joined together with the carbon to which they are both attached to form cyclopropyl or cyclobutyl;

each $R^4$ is independently —H, halo, —CN, —$C_{3-6}$cycloalkyl, —$C(O)OC_{1-4}$alkyl, —$OC_{1-4}$alkyl, or —$C_{1-4}$alkyl optionally substituted with OH or 1-3 of —F;

$R^5$ is —H, halo, or —$C_{1-3}$alkyl optionally substituted with —O—$C_{1-3}$alkyl;

$R^6$ is —H or —$C_{1-3}$alkyl;

$R^7$ is —H or —$C_{1-3}$alkyl optionally substituted with —OH, —$OCH_3$ or 1 to 3 of —F, or $R^7$ is absent when n is zero;

$R^8$ is —H or —$C_{1-3}$alkyl, or $R^8$ is absent when n is zero;

or $R^7$ and $R^8$ are joined together with the carbon to which they are both attached to form cyclopropyl or cyclobutyl;

$R^9$ is —H, halo, —OH, —$C_{1-3}$alkyl, —$OC_{1-3}$alkyl or —$CH_2OH$;

$R^{10}$ is —H, or —$C_{1-3}$alkyl optionally substituted with —OH, —$OCH_3$, or 1 to 3 of —F;

$R^{11}$ is —H, or —$C_{1-3}$alkyl optionally substituted with —OH, —$OCH_3$, or 1 to 3 of —F;

or $R^{10}$ and $R^{11}$ are joined together to represent —$CH_2$—$CH_2$—, —$CH_2$—$N(CH_3)$—$CH_2$— or —$CH_2OCH_2$—;

$R^{12}$, $R^{13}$ and $R^{14}$ are each independently —H, halo, —CN, —$C_{3-6}$cycloalkyl, —$C(O)OC_{1-4}$alkyl, —$OC_{1-4}$alkyl, or —$C_{1-4}$alkyl optionally substituted with —OH or 1-3 of —F;

m is zero where $R^{3b}$ is absent, or one where $R^{3b}$ is present;

the partially dashed double bond ("---") represents a single or double bond wherein:

(i) when m is one, then the dashed bond is a single bond; and (ii) when m is zero and $R^2$ is not =O, then the dashed bond is a double bond; and n is zero or one.

(2) A compound of formula I having structural Formula Ia or a pharmaceutically acceptable salt thereof:

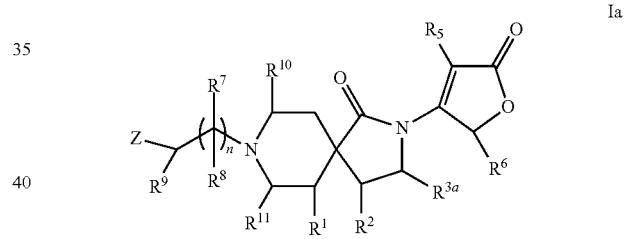

wherein each of the variables n, Z, $R^1$, $R^2$, $R^{3a}$, $R^5$, $R^6$, $R^7$, $R^8$, $R^9$, $R^{10}$, $R^{11}$, and all other variables therein are as defined above in Formula I.

(3) A compound of formula I having structural Formula Ia or a pharmaceutically acceptable salt thereof wherein:

Z is

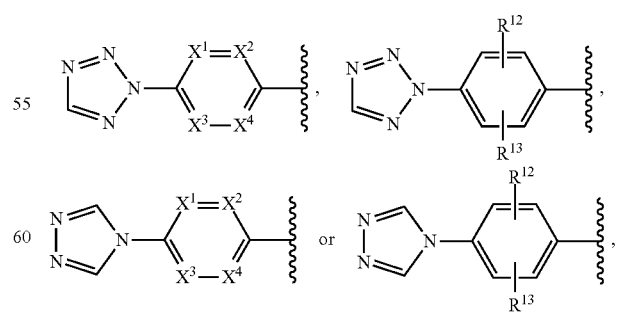

$X^1$, $X^2$, $X^3$ and $X^4$ are each independently selected from $C(R^4)$ and N, provided that at least one and at most two of $X^1$, $X^2$, $X^3$ and $X^4$ are N;

$R^1$ is —H, halo, —OH, or —OC$_{1-3}$alkyl;

$R^2$ is —H, =O (oxo), —OH, —C$_{1-3}$alkyl or —OC$_{1-3}$alkyl;

$R^{3a}$ is —H, —C$_{3-4}$cycloalkyl or —C$_{1-3}$alkyl optionally substituted with —OCH$_3$ or 1 to 3 of —F;

each $R^4$ is independently —H, halo, —CN, —C$_{3-6}$cycloalkyl, —C(O)OC$_{1-4}$alkyl, —OC$_{1-4}$alkyl, or —C$_{1-4}$alkyl optionally substituted with OH or 1-3 of —F;

$R^5$ is —H, halo, or —C$_{1-3}$alkyl optionally substituted with —O—C$_{1-3}$alkyl;

$R^6$ is —H or —C$_{1-3}$alkyl;

$R^7$ is H or —C$_{1-3}$alkyl optionally substituted with —OH, —OCH$_3$ or 1 to 3 of —F, or $R^7$ is absent when n is zero;

$R^8$ is —H or —C$_{1-3}$alkyl, or $R^8$ is absent when n is zero;

$R^9$ is —H, halo, —OH, —C$_{1-3}$alkyl, —OC$_{1-3}$alkyl or —CH$_2$OH;

$R^{10}$ is —H, or —C$_{1-3}$alkyl optionally substituted with —OH, —OCH$_3$, or 1 to 3 of —F;

$R^{11}$ is —H, or —C$_{1-3}$alkyl optionally substituted with —OH, —OCH$_3$, or 1 to 3 of —F;

$R^{12}$ and $R^{13}$ are each independently —H, halo, —CN, —C$_{3-6}$cycloalkyl, —C(O)OC$_{1-4}$alkyl, —OC$_{1-4}$alkyl, or C$_{1-44}$alkyl optionally substituted with —OH or 1-3 of —F; and n is zero or one.

(4) The compound of any of (1)-(3), or a pharmaceutically acceptable salt thereof, wherein:

Z is

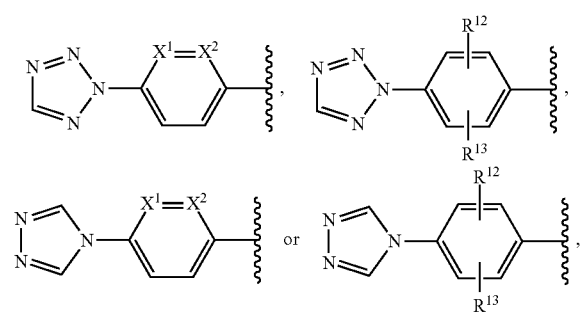

one of $X^1$ or $X^{22}$ is C($R^4$) and the other is N;

$R^1$ is —H, halo, —OH, or —OC$_{1-3}$alkyl;

$R^2$ is —H, =O (oxo), —OH, —C$_{1-3}$alkyl or —OC$_{1-3}$alkyl;

$R^{3a}$ is —H or —C$_{1-3}$alkyl optionally substituted with —OCH$_3$ or 1 to 3 of —F;

each $R^4$ is independently —H, halo, or —C$_{1-4}$alkyl optionally substituted with OH or 1-3 of —F;

$R^5$ is —H, halo, or —C$_{1-3}$alkyl optionally substituted with —O—C$_{1-3}$alkyl;

$R^6$ is —H or —C$_{1-3}$alkyl;

$R^7$ is —H or —C$_{1-3}$alkyl, or $R^7$ is absent when n is zero;

$R^8$ is —H, or $R^8$ is absent when n is zero;

$R^9$ is —H, —F, —OH, —C$_{1-3}$alkyl, —OC$_{1-3}$alkyl or —CH$_2$OH;

$R^{10}$ is —H or —C$_{1-3}$alkyl;

$R^{11}$ is —H or —C$_{1-3}$alkyl;

$R^{12}$, $R^{13}$ and $R^{14}$ are each independently —H, halo, —CN, —C$_{3-6}$cycloalkyl, —C(O)OC$_{1-4}$alkyl, —OC$_{1-4}$alkyl, or —C$_{1-4}$alkyl optionally substituted with —OH or 1-3 of —F; and n is zero or one.

(5) The compound of any of (1)-(4), or a pharmaceutically acceptable salt thereof, wherein:

$R^1$ is —H or halo;

$R^2$ is —H;

$R^{3a}$ is —H or —C$_{1-3}$alkyl;

each $R^4$ is —H;

$R^5$ is —H, halo, or —C$_{1-3}$alkyl;

$R^6$ is —H or —C$_{1-3}$alkyl;

$R^7$ is —H, or $R^7$ is absent when n is zero;

$R^8$ is —H, or $R^8$ is absent when n is zero;

$R^9$ is —H, —F, —OH, —C$_{1-3}$alkyl, —OC$_{1-3}$alkyl or —CH$_2$OH;

$R^{10}$ is —H;

$R^{11}$ is —H;

$R^{12}$, $R^{13}$ and $R^{14}$ are each independently —H, halo, —OC$_{1-4}$alkyl, or —C$_{1-4}$alkyl optionally substituted with —OH or 1-3 of —F; and n is zero or one.

(6) The compound of any of (1)-(5), or a pharmaceutically acceptable salt thereof, wherein Z is:

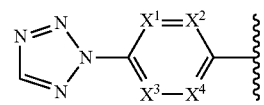

wherein $X^1$, $X^2$, $X^3$ and $X^4$ are as defined therein.

(7) The compound of any of (1)-(5), or a pharmaceutically acceptable salt thereof, wherein Z is:

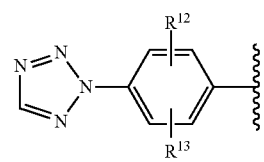

wherein $R^{12}$ and $R^{13}$ are as defined therein.

(8) The compound of any of (1)-(5), or a pharmaceutically acceptable salt thereof, wherein Z is:

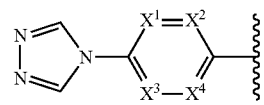

wherein $X^1$, $X^2$, $X^3$ and $X^4$ are as defined therein.

(9) The compound of any of (1)-(5), or a pharmaceutically acceptable salt thereof, wherein Z is:

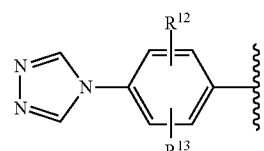

wherein $R^{12}$ and $R^{13}$ are as defined therein.

(10) The compound of any of (1)-(5), or a pharmaceutically acceptable salt thereof, wherein Z is:

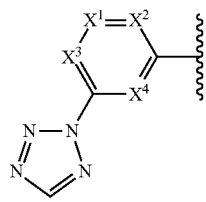

wherein $X^1$, $X^2$, $X^3$ and $X^4$ are as defined therein.

(11) The compound of any of (1)-(5), or a pharmaceutically acceptable salt thereof, wherein Z is:

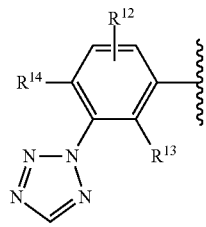

wherein $R^{12}$, $R^{13}$ and $R^{14}$ are as defined therein.

(12) The compound of any of (1)-(5), or a pharmaceutically acceptable salt thereof, wherein Z is:

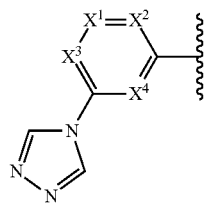

wherein $X^1$, $X^2$, $X^3$ and $X^4$ are as defined therein.

(13) The compound of any of (1)-(5), or a pharmaceutically acceptable salt thereof, wherein Z is:

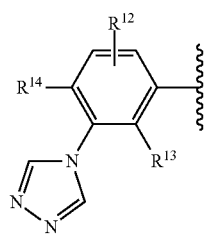

wherein $R^{12}$ $R^{13}$ and $R^{14}$ are as defined therein.

(14) The compound of any of (1)-(4) and (6)-(13), or a pharmaceutically acceptable salt thereof, wherein $R^1$ is H, —$OCH_3$ or F, and more particularly it is —H.

(15) The compound of any of (1)-(14), or a pharmaceutically acceptable salt thereof, wherein $R^1$ is —H.

(16) The compound of any of (1)-(4) and (6)-(15), or a pharmaceutically acceptable salt thereof, wherein $R^2$ is —H, —OH, =O, —$CH_3$ or —$OCH_3$.

(17) The compound of any of (1)-(16), or a pharmaceutically acceptable salt thereof, wherein $R^2$ is —H.

(18) The compound of any of (1)-(4) and (6)-(17), or a pharmaceutically acceptable salt thereof, wherein $R^{3a}$ is —H, —$C_{1-3}$alkyl, or cyclopropyl.

(19) The compound of any of (1)-(17), or a pharmaceutically acceptable salt thereof, wherein $R^{3a}$ is —H or —$CH_3$.

(20) The compound of (1), or a pharmaceutically acceptable salt thereof, wherein $R^{3b}$ is —H or —$C_{1-3}$alkyl.

(21) The compound of (1), or a pharmaceutically acceptable salt thereof, wherein $R^{3b}$ is —H or absent when the dashed double bond is a double bond.

(22) The compound of any of (1)-(3) and (6)-(21), or a pharmaceutically acceptable salt thereof, wherein each $R^4$ is independently —H, —F, —Cl, —C(O)$OCH_3$, —$C_{3-4}$cycloalkyl particularly cyclopropyl, —$OCH_3$, or —$C_{1-3}$alkyl optionally substituted with —OH or 1-3 of —F, and particularly each $R^4$ is —H or —$C_{1-3}$alkyl. In particular embodiments, at least one $R^4$ is —H.

(23) The compound of any of (1)-(4) and (6)-(22), or a pharmaceutically acceptable salt thereof, wherein $R^5$ is —H, halo particularly —F or —Cl, or —$C_{1-3}$alkyl, and more particularly it is —H or —$CH_3$.

(24) The compound of any of (1)-(23), or a pharmaceutically acceptable salt thereof, wherein $R^6$ is —H or —$CH_3$, and more particularly it is —H.

(25) The compound of any of (1)-(3) and (6)-(24), or a pharmaceutically acceptable salt thereof, wherein $R^7$, when present, is —H, —$CH_3$ or —$CH_2OH$, and more particularly it is —H or —$CH_3$.

(26) The compound of any of (1)-(3) and (6)-(25), or a pharmaceutically acceptable salt thereof, wherein $R^8$, when present, is —H or —$CH_3$, more particularly it is —H.

(27) The compound of any of (1)-(26), or a pharmaceutically acceptable salt thereof, wherein $R^9$—H, —OH, —$OCH_3$, or —$CH_2OH$, and particularly it is —H or —OH.

(28) The compound of any of (1)-(3) and (6)-(27), or a pharmaceutically acceptable salt thereof, wherein $R^{10}$ is —H, —$CH_2OH$, —$CH_2OCH_3$, or —$C_{1-3}$alkyl optionally substituted with 1 to 3 of —F, particularly —H or $CH_3$, and more particularly —H.

(29) The compound of any of (1)-(3) and (6)-(28), or a pharmaceutically acceptable salt thereof, wherein $R^{11}$ is —H, —$CH_2OH$, —$CH_2OCH_3$, or —$C_{1-3}$alkyl optionally substituted with 1 to 3 of —F, particularly —H or —$CH_3$, and more particularly —H.

(30) The compound of any of (1)-(29), or a pharmaceutically acceptable salt thereof, wherein $R^{12}$, $R^{13}$ and $R^{14}$ are each independently —H, —F, —Cl, —$CF_3$, —$C_{1-3}$alkyl or —$OC_{1-3}$alkyl.

(31) The compound of any of (1)-(30), or a pharmaceutically acceptable salt thereof, wherein n is one.

(32) The compound of (1)-(24) and (27)-(30), or a pharmaceutically acceptable salt thereof, wherein n is zero.

(33) A compound of formula I which is elsewhere disclosed herein or is:

8-(2-(4-(2H-tetrazol-2-yl)phenyl)-2-hydroxyethyl)-2-(4-methyl-5-oxo-2,5-dihydrofuran-3-yl)-2,8-diazaspiro[4.5]decan-1-one;

8-(2-(4-(4H-1,2,4-triazol-4-yl)phenyl)-2-hydroxyethyl)-2-(4-methyl-5-oxo-2,5-dihydrofuran-3-yl)-2,8-diazaspiro[4.5]decan-1-one;

8-(2-(6-(4H-1,2,4-triazol-4-yl)pyridin-3-yl)-2-hydroxyethyl)-2-(4-methyl-5-oxo-2,5-dihydrofuran-3-yl)-2,8-diazaspiro[4.5]decan-1-one;

(S)-8-(2-(4-(2H-tetrazol-2-yl)phenyl)-2-hydroxyethyl)-2-(4-methyl-5-oxo-2,5-dihydrofuran-3-yl)-2,8-diazaspiro[4.5]decan-1-one;

(S)-8-((S)-2-(4-(2H-tetrazol-2-yl)phenyl)-2-hydroxyethyl)-3-methyl-2-(5-oxo-2,5-dihydrofuran-3-yl)-2,8-diazaspiro[4.5]decan-1-one;

(S)-8-((R)-2-(4-(2H-tetrazol-2-yl)phenyl)-2-hydroxyethyl)-3-methyl-2-(5-oxo-2,5-dihydrofuran-3-yl)-2,8-diazaspiro[4.5]decan-1-one;

or a pharmaceutically acceptable salt thereof.

The compounds of the present invention are further described herein using the terms defined below unless otherwise specified.

"Alkyl", as well as other groups having the prefix "alk", such as alkoxy, and the like, means carbon chains which may be linear or branched, or combinations thereof, containing the indicated number of carbon atoms. Examples of alkyl groups include methyl, ethyl, propyl, isopropyl, butyl, sec- and tert-butyl, pentyl, hexyl, heptyl, octyl, nonyl and the like. In specific embodiments, alkyl means a linear or branched $C_{1-6}$ or $C_{1-3}$alkyl.

"Alkoxy" refers to an alkyl group linked to oxygen. In specific embodiments, alkoxy means a linear or branched $C_{1-6}$ or $C_{1-3}$alkoxy in which the point of attachment is at oxygen.

"Cycloalkyl" means a saturated cyclic hydrocarbon radical having the number of carbon atoms designated. Examples of cycloalkyl include cyclopropyl, cyclobutyl, cyclopentyl and cyclohexyl. In specific embodiments, cycloalkyl means a $C_{3-6}$ or $C_{3-4}$cycloalkyl. In particular embodiments, cycloalkyl means $C_3$cycloalkyl (or cyclopropyl).

"Halogen" or "halo" includes fluorine, chlorine, bromine and iodine.

Unless expressly depicted or described otherwise, variables depicted in a structural formula with a "floating" bond, such as substituents $R^{12}$ and $R^{13}$, are permitted on any available carbon atom in the ring to which each is attached.

Substitution, where applicable, may be on any available carbon atom that results in a stable structure.

Also, number ranges where provided (e.g., 1-6) expressly include each and every number in that range as a discrete embodiment.

Atoms of the compounds described herein may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of any of (1)-(33). For example, different isotopic forms of hydrogen (H) include protium (1H) and deuterium (2H). Protium is the predominant hydrogen isotope found in nature. Enriching for deuterium may yield certain therapeutic advantages, such as increasing in vivo half-life or reducing dosage requirements, or may provide a compound useful as a standard for characterization of biological samples. Isotopically-enriched compounds of any of (1)-(33) described herein can be prepared without undue experimentation by conventional techniques well known to those skilled in the art or by processes analogous to those described in the Examples herein using appropriate isotopically-enriched reagents and/or intermediates.

Individual tautomers of the compounds of any of (1)-(33), as well as mixtures thereof, are encompassed herein. Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers.

Compounds described herein may contain an asymmetric center and may thus exist as enantiomers. Where the compounds according to the invention possess two or more asymmetric centers, they may additionally exist as diastereomers. When bonds to the chiral carbon are depicted as straight lines in the formulas of the invention, it is understood that both the (R) and (S) configurations of the chiral carbon, and hence both enantiomers and mixtures thereof, are embraced. The present invention includes all such possible stereoisomers as substantially pure resolved enantiomers, racemic mixtures thereof, as well as mixtures of diastereomers. Except where otherwise specified, the formulae encompassing compounds of the present invention are shown without a definitive stereochemistry at certain positions. The present invention therefore may be understood to include all stereoisomers of compounds of any of (1)-(33) and pharmaceutically acceptable salts thereof.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of any of (1)-(33) may be obtained by stereospecific synthesis using optically pure starting materials or reagents of known configuration.

Furthermore, some of the crystalline forms for compounds of the present invention may exist as polymorphs and as such are intended to be included in the present invention. In addition, some of the compounds of the instant invention may form solvates with water or common organic solvents. Solvates, and in particular, the hydrates of the compounds of any of (1)-(33) are also included in the present invention.

The term "pharmaceutically acceptable salt" refers to a salt prepared from pharmaceutically acceptable non-toxic bases or acids including inorganic bases or acids and organic bases or acids.

Salts of basic compounds encompassed within the term "pharmaceutically acceptable salt" refer to non-toxic salts of the compounds described herein which are generally prepared by reacting the free base with a suitable organic or inorganic acid. Representative salts of basic compounds described herein include, but are not limited to, the following: acetate, benzenesulfonate, benzoate, bicarbonate, bisulfate, bitartrate, borate, bromide, camsylate, carbonate, chloride, clavulanate, citrate, edetate, edisylate, estolate, esylate, formate, fumarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, palmitate, pamoate (embonate), pantothenate, phosphate/diphosphate, polygalacturonate, salicylate, stearate, sulfate, subacetate, succinate, tannate, tartrate, teoclate, tosylate, triethiodide and valerate. Furthermore, where the compounds described herein carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. In particular embodiments, the salt is selected from ammonium, calcium, magnesium, potassium, or sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

The compounds of Formula I according to the invention are inhibitors of ROMK, and therefore could be used as diuretic and/or natriuretic agents. ROMK inhibitors may be used to help to increase urination and increase urine volume and also to prevent or reduce reabsorption of sodium in the kidneys leading to increased excretion of sodium and water. Therefore, the compounds could be used for treatment or prophylaxis or both of disorders that benefit from increased excretion of water and sodium from the body. Accordingly, the compounds of this invention could be used in a method for inhibiting ROMK comprising administering a compound of Formula I in a ROMK-inhibitory effective amount to a patient in need thereof. This also encompasses the use of the compounds for inhibiting ROMK in a patient comprising administering a compound of claim 1 in a therapeutically effective amount to a patient in need of diuresis, natriuresis or both. The inhibition of ROMK by the compounds of Formula I can be examined, for example, in the Thallium Flux Assay described below. Moreover, this invention also relates to the use of the compounds of Formula I or salts thereof to validate in vitro assays, for example but not limited to the Thallium Flux Assay described herein.

The compounds of this invention could be used in a method for causing diuresis, natriuresis or both, comprising administering a compound of Formula I in a therapeutically effective amount to a patient in need thereof. Therefore, the compounds of Formual I of this invention could be used in methods for treatment of, prevention of or reduction of risk for developing medical conditions that benefit from increased excretion of water and sodium, such as but not limited to one or more of hypertension, such as essential hypertension (also known as primary or idiopathic hypertension) which is a form of hypertension for which no cause can be found, heart failure (which includes both acute heart failure and chronic heart failure, the latter also known as congestive heart failure) and/or other conditions associated with excessive salt and water retention. The compounds could also be used to treat hypertension which is associated with any of several primary diseases, such as renal, pulmonary, endocrine, and vascular diseases, including treatment of patients with medical conditions such as heart failure and/or chronic kidney disease. Furthermore, the compounds of Formula I could be used in methods for treatment of, prevention of or reduction of risk for developing one or more disorders such as pulmonary hypertension, particularly pulmonary arterial hypertension (PAH), cardiovascular disease, edematous states, diabetes mellitus, diabetes insipidus, post-operative volume overload, endothelial dysfunction, diastolic dysfunction, systolic dysfunction, stable and unstable angina pectoris, thromboses, restenosis, myocardial infarction, stroke, cardiac insufficiency, pulmonary hypertonia, atherosclerosis, hepatic cirrhosis, ascites, pre-eclampsia, cerebral edema, nephropathy, glomerulonephritis, nephrotic syndrome, acute kidney insufficiency, chronic kidney insufficiency (also referred to as chronic kidney disease, or more generally as renal impairment), acute tubular necrosis, hypercalcemia, idiopathic edema, Dent's disease, Meniere's disease, glaucoma, benign intracranial hypertension, and other conditions for which a diuretic or natriuretic or both would have therapeutic or prophylactic benefit. The compounds of the invention may be administered to a patient having, or at risk of having, one or more conditions for which a diuretic or natriuretic or both would have therapeutic or prophylactic benefit such as those described herein.

The compounds of Formula I may potentially have reduced liabilities (for example, hypo- or hyperkalemia, new onset of diabetes, dyslipidemia, etc.) over currently used clinical agents. Also the compounds may have reduced risk for diuretic tolerance, which can be a problem with long-term use of loop diuretics.

In general, compounds that are ROMK inhibitors can be identified as those compounds which, when tested, have an IC50 of 5 μM or less, preferably 1 μM or less, and more particularly 0.25 μM or less, in the Thallium Flux Assay, described in more detail further below.

The dosage amount of the compound to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I. A consideration of these factors is well within the purview of the ordinarily skilled clinician for the purpose of determining the therapeutically effective or prophylactically effective dosage amount needed to prevent, counter, or arrest the progress of the condition. It is expected that the compound will be administered chronically on a daily basis for a length of time appropriate to treat or prevent the medical condition relevant to the patient, including a course of therapy lasting days, months, years or the life of the patient.

In general, a daily dose of approximately 0.001 to 100 mg/kg, particularly 0.001 to 30 mg/kg, in particular 0.001 to 10 mg/kg (in each case mg per kg of bodyweight) is appropriate for administration to an adult weighing approximately 75 kg in order to obtain the desired results. The daily dose is particularly administered in a single dose or can be divided into several, for example two, three or four individual doses, and may be, for example but not limited to, 0.1 mg, 0.25 mg, 0.5 mg, 0.75 mg, 1 mg, 1.25 mg, 2 mg, 2.5 mg, 5 mg, 10 mg, 20 mg, 40 mg, 50 mg, 75 mg, 100 mg, 125 mg, 150 mg, 175 mg, 200 mg, etc., on a daily basis. In some cases, depending on the potency of the compound or the individual response, it may be necessary to deviate upwards or downwards from the given daily dose. Furthermore, the compound may be formulated for immediate or modified release such as extended or controlled release.

The term "patient" includes animals, particularly mammals and especially humans, who use the instant active agents for the prophylaxis or treatment of a medical condition. Administering of the drug to the patient includes both self-administration and administration to the patient by another person. The patient may be in need of treatment for an existing disease or medical condition, or may desire prophylactic treatment to prevent or reduce the risk for developing said disease or medical condition or developing long-term complications from a disease or medical condition.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician. A "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. The terms "preventing," "prevention," "prophylactic" and derivatives of these terms as used herein refer to administering a compound to a patient before the onset of clinical symptoms of a condition not yet present in the patient. It is understood that a specific daily dosage amount can simultaneously be both a therapeutically effective amount, e.g., for treatment of hypertension, and a prophylactically effective amount, e.g., for prevention or reduction of risk of myocardial infarction or prevention or reduction of risk for complications related to hypertension.

In the methods of treatment of this invention, the ROMK inhibitors may be administered via any suitable route of administration such as, for example, orally, parenterally, or rectally in dosage unit formulations containing conventional non-toxic pharmaceutically acceptable carriers, adjuvants and vehicles. The term parenteral as used herein includes subcutaneous injections, intravenous (IV), intramuscular, intrasternal injection or infusion techniques. Oral formulations are preferred for treatment of chronic indications such as hypertension or chronic heart failure, particularly solid oral dosage units such as pills, tablets or capsules, and more particularly tablets. IV dosing is preferred for acute treatment, for example for the treatment of acute heart failure.

This invention also provides pharmaceutical compositions comprised of a compound of Formula I and a pharmaceutically acceptable carrier which is comprised of one or more excipients or additives. An excipient or additive is an inert substance used to formulate the active drug ingredient. For oral use, the pharmaceutical compositions of this invention containing the active ingredient may be in forms such as pills, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Tablets contain the active ingredient in admixture with non-toxic pharmaceutically acceptable excipients which are suitable for the manufacture of tablets. The excipients may be for example, inert diluents, such as calcium carbonate, sodium carbonate, lactose, mannitol, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc.

Pharmaceutical compositions may also contain other customary additives, for example but not limited to, wetting agents, stabilizers, emulsifiers, dispersants, preservatives, sweeteners, colorants, flavorings, aromatizers, thickeners, buffer substances, solvents, solubilizers, agents for achieving a depot effect, salts for altering the osmotic pressure, coating agents or antioxidants. Oral immediate-release and time-controlled release dosage forms may be employed, as well as enterically coated oral dosage forms. Tablets may be uncoated or they may be coated by known techniques for aesthetic purposes, to mask taste or for other reasons. Coatings can also be used to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an anti-oxidant such as ascorbic acid. Syrups and elixirs may be formulated with sweetening agents, for example glycerol, propylene glycol, sorbitol or sucrose.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier. Furthermore, a therapeutically effective amount of a compound of this invention can be used for the preparation of a medicament useful for inhibiting ROMK, for causing diuresis and/or natriuresis, and/or for treating, preventing or reducing the risk for any of the medical conditions described herein, in dosage amounts described herein.

The amount of active compound of Formula I and/or its pharmaceutically acceptable salts in the pharmaceutical composition may be, for example but not limited to, from about 0.1 mg to 1 g, particularly 0.1 mg to about 200 mg, more particularly from about 0.1 mg to about 100 mg, and even more particularly from about 0.1 to about 50 mg, per dose on a free acid/free base weight basis, but depending on the type of the pharmaceutical composition, potency of the active ingredient and/or the medical condition being treated, it could also be lower or higher. Pharmaceutical compositions usually comprise about 0.5 to about 90 percent by weight of the active compound on a free acid/free base weight basis.

The compounds of Formula I inhibit ROMK. Due to this property, apart from use as pharmaceutically active compounds in human medicine and veterinary medicine, they can also be employed as a scientific tool or as aid for biochemical investigations in which such an effect on ROMK is intended, and also for diagnostic purposes, for example in the in vitro diagnosis of cell samples or tissue samples. The compounds of Formula I can also be employed as intermediates for the preparation of other pharmaceutically active compounds.

One or more additional pharmacologically active agents may be administered in combination with a compound of Formula I. The additional active agent (or agents) is intended to mean a medicinal compound that is different from the compound of Formula I, and which is a pharmaceutically active agent (or agents) that is active in the body, including pro-drugs, for example esterified forms, that convert to pharmaceutically active form after administration, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents). Examples of the one or more additional active agents which may be employed include but are not limited to thiazide-like diuretics, e.g., hydrochlorothiazide (HCTZ or HCT); angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); dual inhibitors of angiotensin converting enzyme (ACE) and neutral endopeptidase (NEP) such as omapatrilat, sampatrilat and fasidotril; angiotensin II receptor antagonists, also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, epleranone, triamterene, each with or without HCTZ; carbonic anhydrase inhibitors, such as acetazolamide; neutral endopeptidase inhibitors (e.g., thiorphan and phosphoramidon); aldosterone antagonists; aldosterone synthase inhibitors; renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643); enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine, bepridil, nisoldipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); nitrates or nitric oxide donating compounds, e.g. isosorbide mononitrate; lipid lowering agents, e.g., HMG-CoA reductase inhibitors such as simvastatin and lovastatin which are marketed as ZOCOR® and MEVACOR® in lactone prodrug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; phosphodiesterase-5 (PDE5) inhibitors such as sildenafil (Revatio, Viagra), tadalafil (Cialis, Adcirca) vardenafil HCl (Levitra); or with other drugs beneficial for the prevention or the treatment of the above-mentioned diseases including but not limited to diazoxide; and including the free-acid, free-base, and pharmaceutically acceptable salt forms, pro-drug forms (including but not limited to esters), and salts of pro-drugs of the above medicinal agents where chemically possible. Trademark names of pharmaceutical drugs noted above are provided for exemplification of the marketed form of the active agent(s); such pharmaceutical drugs could be used in a separate dosage form for concurrent or sequential administration with a compound of Formula I, or the active agent(s) therein could be used in a fixed dose drug combination including a compound of Formula I.

EXAMPLES

Several methods for preparing the compounds of this invention are described in the following Schemes and Examples. Starting materials and intermediates are purchased, made from known procedures, or as otherwise illustrated. Some frequently applied routes to the compounds of Formula I are also described by the Schemes as follows. In some cases the order of carrying out the steps of reaction schemes may be varied to facilitate the reaction or to avoid unwanted reaction products. The "R" substituents in the Schemes correspond to the substituents defined in Formula I at the same positions on the structures. The ring structure:

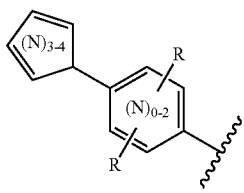

is intended to represent each of the individual groups of Z as defined in Formula I.

Compound 1.3, which is substituted at the benzylic position with an OH group, can be prepared following the sequence detailed in Scheme 1. Coupling of epoxides 1.1 to spirocyclic amines 1.2 at elevated temperatures leads to the formation of alcohols 1.3 as the major product and alcohols 1.4 as a minor side product (Nomura, Y. et al. Chemical & Pharmaceutical Bulletin, 1995, 43(2), 241-6). The reaction can be carried out with conventional heating, or by heating using a microwave apparatus. A number of solvents can be used in this reaction, for example, ethanol and 2-propanol. Spirocyclic amines may be free bases, or they may be salts, in which case a base such as triethylamine or N;N-diisopropylethylamine may be added. Note that when enantiomerically pure chiral epoxides are employed the epoxide opening occurs with retention of stereochemistry in the benzylic position and the individual isomer may be obtained. Alternatively, chiral HPLC separation of enantiomers or diastereomers of 1.3 or 1.4 may be performed to provide single enantiomers or diastereomers.

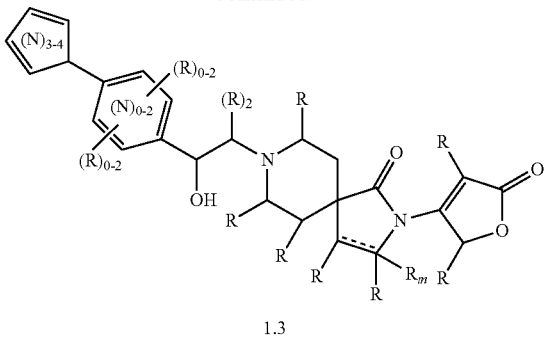

1.3

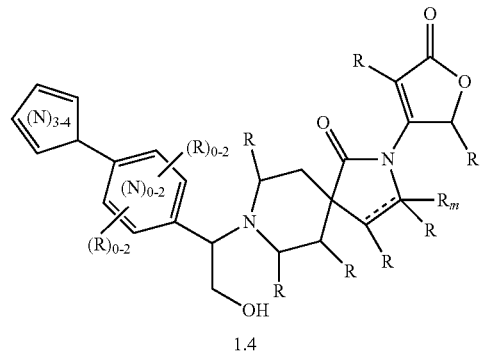

1.4

Compounds of formula 2.2 can be prepared by the sequence detailed in Scheme 2. Aldehydes or ketones 2.1 may be used in reductive alkylation reactions of spirocyclic amines 1.2 by using various reductive amination conditions (e.g., using sodium cyanoborohydride, sodium triacetoxy borohydride, or titanium tetra-isopropoxide, followed by sodium borohydride or sodium cyanoborohydride).

SCHEME 1

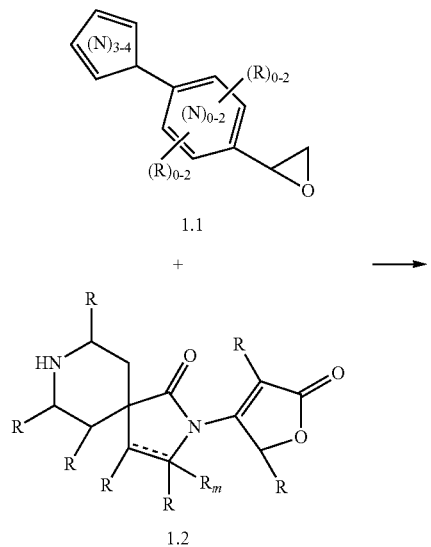

SCHEME 2

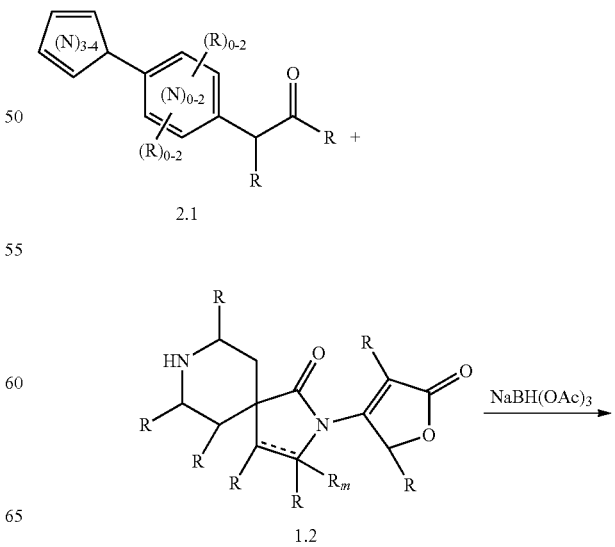

-continued

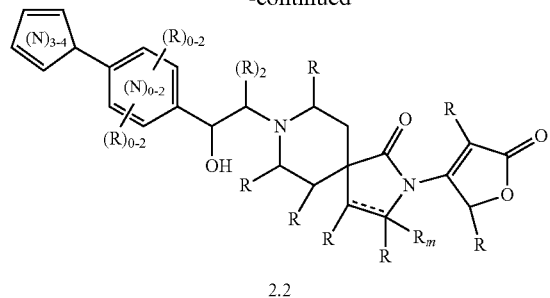

2.2

-continued

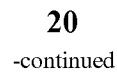
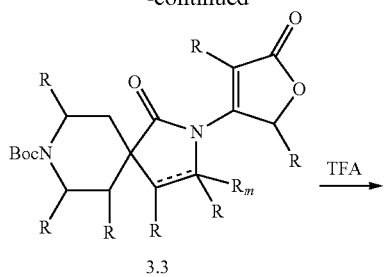

3.3

Spirocyclic amidofuranones 1.2 can be prepared as described in Scheme 3. Spirocyclic amino lactams 3.1 may be coupled to furanone triflates or bromides 3.2 using a palladium catalyst and ligand, for example palladium acetate and 4,5-bis(diphenylphosphino)-9,9-dimethylxanthene. Some spirocyclic amino lactams 3.1 described herein are commercially available, others can be prepared as described in the experimental section below. 4-Bromofuran-2(5H)-one is commercially available, other furanones can be prepared as described in the examples below. Intermediates 3.3 are converted to spirocyclic amidofuranones 1.2 by removal of the protective group, for example, tert-butoxycarbonyl can be removed with TFA or HCl.

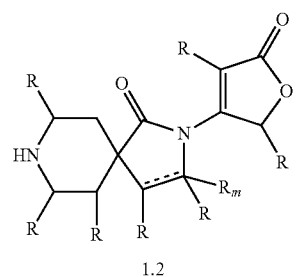

1.2

Spirocyclic amino lactams 4.4, can be prepared in numerous ways, including those described in Scheme 4. Commercially available aminoesters 4.1 can be alkylated with bromoacetonitrile 4.2 using a base such as lithium diisopropylamide to afford nitrile intermediates 4.3. Reduction, for example using hydrogenation in the presence of platinum oxide, or Raney Nickel, produces lactams 4.4. Alternatively, aminoesters 4.1 may be alkylated with allyl halides 4.5 using a base such as lithium diisopropylamide to furnish allyl intermediates 4.6. Oxidative cleavage, employing, for example, osmium tetraoxide and sodium periodate provides ketones or aldehydes 4.7. Reductive amination with tandem lactam cyclization to 4.4 can be accomplished in several ways, including by treatment with ammonium acetate and sodium cyanoborohydride in a solvent such as methanol, as shown.

SCHEME 3

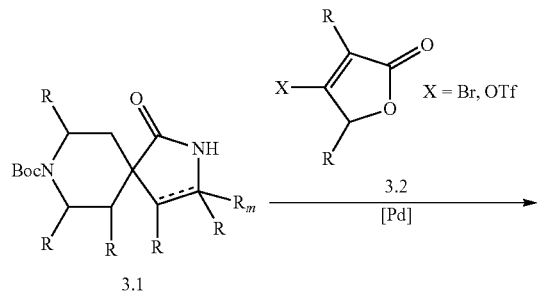

SCHEME 4

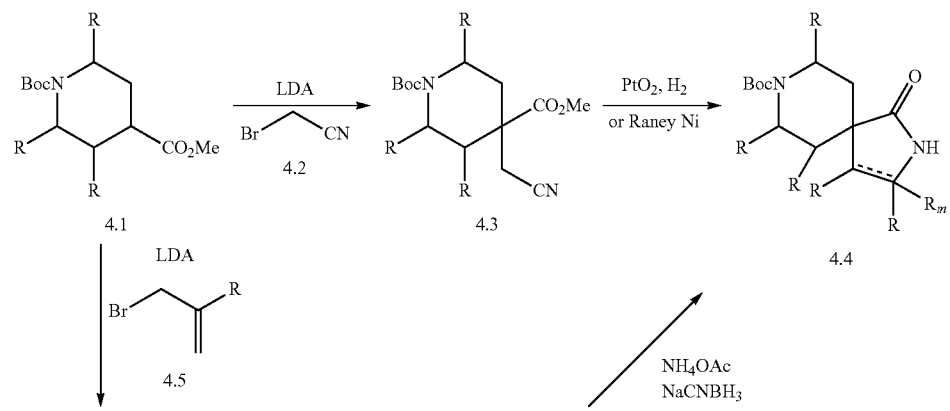

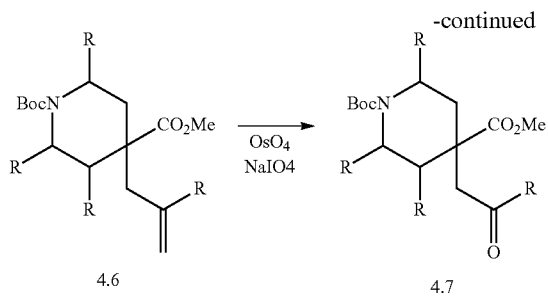

Scheme 5 shows preparation of spirocyclic furanone intermediates 5.5A and 5.5B. Commercially available aminoesters 5.1 can be alkylated with bromoacetonitrile using a base such as KHMDS to afford nitrile intermediates 5.2. Reduction, for example using platinum oxide and hydrogen, produces aminoalcohols 5.3, which was cyclized with ammonia in methanol to give lactams 5.4. Coupling of lactams 5.4 with furanone triflates or bromides using a palladium catalyst and ligand followed by column separation generates intermediates trans-isomers 5.5A and cis-isomers 5.5B.

SCHEME 5

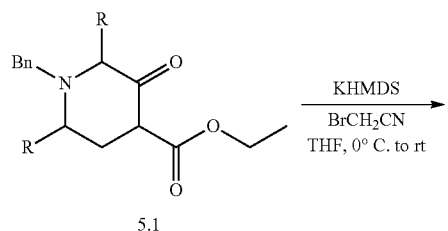

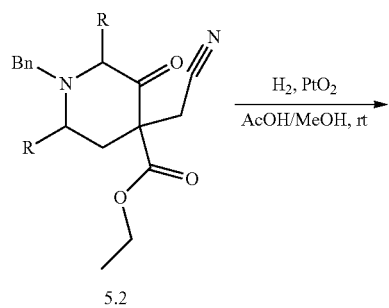

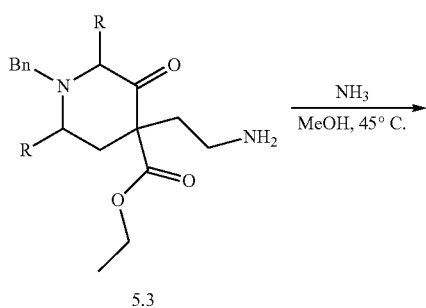

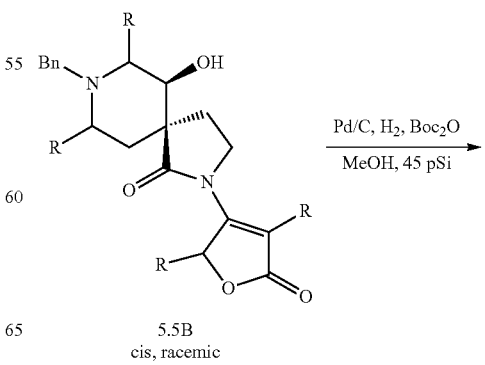

Preparation of intermediates 6.3A and 6.3B is accomplished as described in Scheme 6. The benzyl-protection group in cis racemic alcohols 5.5B is replaced by a BOC group. The BOC-protected compounds of type 6.1 can then be transformed to trans-racemic fluorides 6.2 which are separated by chiral column, and subsequent deprotected of the BOC group with TFA in DCM to give intermediates of type 6.3.

SCHEME 6

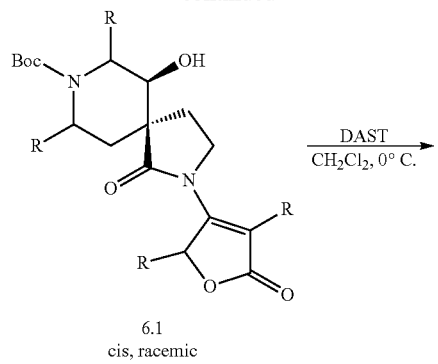

6.1
cis, racemic

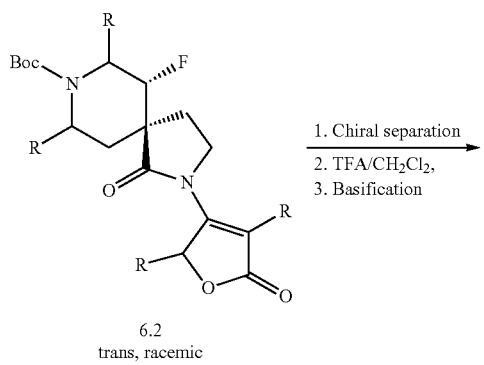

6.2
trans, racemic

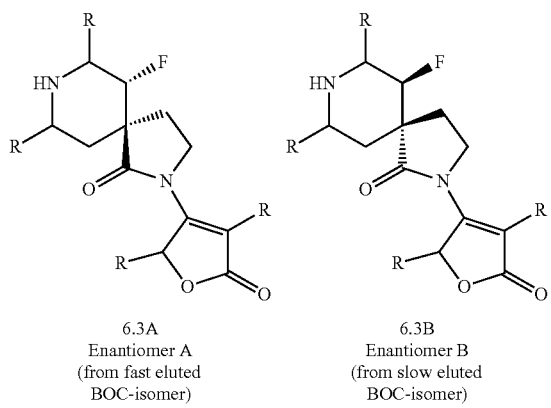

6.3A
Enantiomer A
(from fast eluted BOC-isomer)

6.3B
Enantiomer B
(from slow eluted BOC-isomer)

Preparation of tetrazole-epoxide intermediates of type 1.1 may start from halo-substituted aniline 7.1 (Scheme 7). The epoxide ring in intermediate 1.1 can be built by treatment of 7.1 (where X is chloride, bromide, iodide, or trifluoromethane sulfonate) with potassium vinyl trifluoroborate (Molander, G.; Luciana, A. Journal of Organic Chemistry, 2005, 70(10), 3950-3956) under palladium catalyzed coupling conditions followed by epoxidation of the formed styrene (7.2) with NBS/NaOH. Alternatively, other methods for formation of styrene may be employed, for example, using vinylstannane reagents and palladium catalyst, and other methods for epoxidation of the styrene may use, for example, m-CPBA. The racemic epoxides of formula 1.1 can be resolved under chiral HPLC chromatography conditions to afford its enantiomers (R)-7.3A and (S)-7.3B.

SCHEME 7

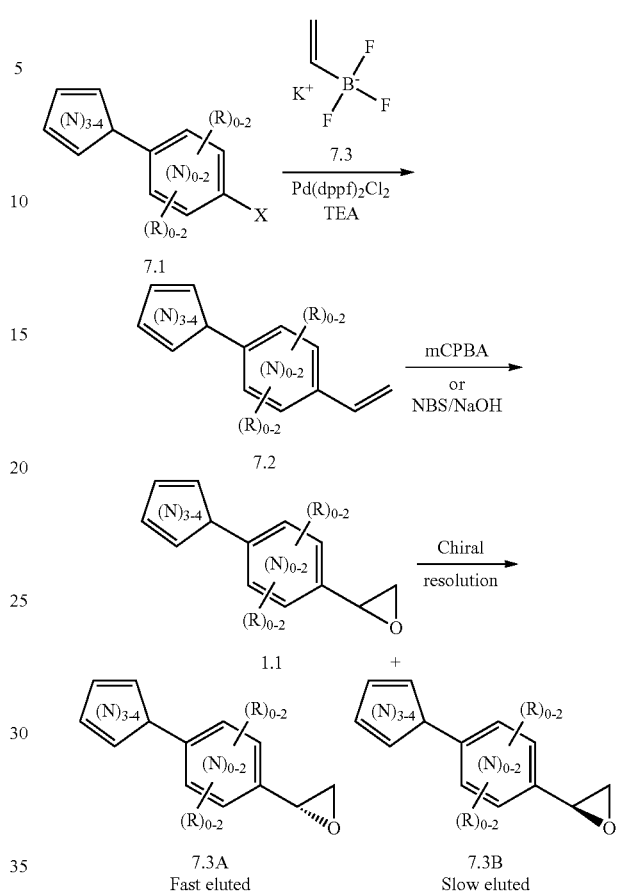

Preparation of triazole-arylhalide intermediates of type 8.2 may start from halo-substituted aniline 8.1 (Scheme 8; X=halo). Thus, formation of the triazole ring can be accomplished by condensation of halo-substituted aniline 8.1 with N'-formylformohydrazide at 170° C.

SCHEME 8

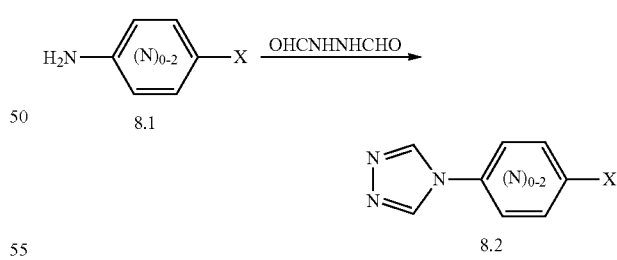

The formation of the tetrazole ring in halo-substituted tetrazolo[1,5-a]quinoline intermediates of type 9.2 can be accomplished by cyclization of 6-halo-substituted quinoline 9.1 or 6-halo-subsituted-2-chloroquinoline 9.3 (Scheme 9) with sodium azide at elevated temperature such as 130° C.

The independent synthesis of diastereomers and enantiomers or their chromatographic separations may be achieved as known in the art by appropriate modification of the methodology disclosed herein. Their absolute stereochemistry may be determined by x-ray crystallography of crystalline products or crystalline intermediates which are derivatized, if necessary, with a reagent containing an asymmetric center of known absolute stereochemistry, or by vibrational circular dichroism (VCD) spectroscopy.

The subject compounds may be prepared by modification of the procedures disclosed in the Examples as appropriate. Starting materials are commercially available or made by known procedures or as illustrated.

Reactions sensitive to moisture or air were performed under nitrogen or argon using anhydrous solvents and reagents. The progress of reactions was determined by either analytical thin layer chromatography (TLC) usually performed with E. Merck pre-coated TLC plates, silica gel 60E-254, layer thickness 0.25 mm or liquid chromatography-mass spectrometry (LC-MS).

Typically the analytical LC-MS system used consisted of a WATERS ZQ platform with electrospray ionization in positive ion detection mode with an Agilent 1100 series HPLC with autosampler. The column was usually a WATERS XTERRA MS C18, 3.0×50 mm, 5 µm. The flow rate was 1 mL/min, and the injection volume was 10 µL. UV detection was in the range 210-400 nm. The mobile phase consisted of solvent A (water plus 0.05% TFA) and solvent B (acetonitrile plus 0.05% TFA) with a gradient of 100% solvent A for 0.7 min changing to 100% solvent B over 3.75 min, maintained for 1.1 min, then reverting to 100% solvent A over 0.2 min.

Preparative HPLC purifications were usually performed using a mass spectrometry directed system. Usually they were performed on a WATERS Chromatography Workstation configured with an LC-MS System consisting of: WATERS ZQ single quad MS system with Electrospray Ionization, WATERS 2525 Gradient Pump, WATERS 2767 Injector/Collector, WATERS 996 PDA Detector, the MS Conditions of: 150-750 amu, Positive Electrospray, Collection Triggered by MS, and a WATERS SUNFIRE C-18 5 micron, 30 mm (id)×100 mm column. The mobile phases consisted of mixtures of acetonitrile (10-100%) in water containing 0.1% TFA. Flow rates were maintained at 50 mL/min, the injection volume was 1800 µL, and the UV detection range was 210-400 nm. Mobile phase gradients were optimized for the individual compounds.

Reactions performed using microwave irradiation were normally carried out using an Emrys Optimizer manufactured by Personal Chemistry, or an Initiator manufactured by BIOTAGE.

Concentration of solutions was carried out on a rotary evaporator under reduced pressure. Flash chromatography was usually performed using a BIOTAGE Flash Chromatography apparatus (Dyax Corp.) on silica gel (32-63 mM, 60 Å pore size) in pre-packed cartridges of the size noted. $^1$H NMR spectra were acquired at 500 MHz spectrometers in CDCl$_3$ solutions unless otherwise noted. Chemical shifts were reported in parts per million (ppm). Tetramethylsilane (TMS) was used as the internal reference in CDCl$_3$ solutions, and residual CH$_3$OH peak or TMS was used as the internal reference in CD$_3$OD solutions. Coupling constants (J) were reported in hertz (Hz).

Chiral analytical chromatography was usually performed on one of CHIRALPAK AS, CHIRALPAK AD, CHIRALCEL OD, CHIRALCEL IA, or CHIRALCEL OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was sometimes conducted on one of CHIRALPAK AS, CHIRALPAK AD, CHIRALCEL OD, CHIRALCEL IA, or CHIRALCEL OJ columns (20×250 mm) (Daicel Chemical Industries, Ltd.) with desired isocratic solvent systems identified on chiral analytical chromatography or by supercritical fluid (SFC) conditions. Alternatively, chiral preparative chromatography was conducted by supercritical fluid (SFC) conditions using one of CHIRALPAK AS, CHIRALPAK AD-H, CHIRALCEL OD-H, CHIRALPAK IC, or CHIRALCEL OJ-H columns (250×21.2 mm) (Daicel Chemical Industries, Ltd.). Where retention times are provided in the Examples and Tables, they are not intended to be a definitive characteristic of a particular compound since, as known to those skilled in the art, retention times will vary and the timing and/or order of peak elution may change depending on the chromatographic conditions, such as the column used, the condition of the column, and the solvent system and instruments used.

Flash chromatography was carried out on silica gel (230-400 mesh). NMR spectra were obtained in CDCl$_3$ solution unless otherwise noted. Coupling constants (J) are in hertz (Hz).

Abbreviations used herein include: —C(O)CH$_3$ (Ac); acetic acid (AcOH; HOAc); —OC(O)CH$_3$ (OAc); aqueous (aq); benzyl (bn); benzyloxycarbonyl (Cbz); 3-chloroperoxybenzoic acid (mCPBA); Dess-Martin Periodinane (DMP); 1,1,1-Triacetoxy-1,1-dihydro-1,2,benziodoxol-3 (1H)-one; deuterated chloroform (CDCl$_3$); dibenzylideneacetone (dba); diethyl amine (DEA); di-t-butyl dicarbonate ((BOC)$_2$O, Boc$_2$O); 1,8-Diazabicyclo[5.4.0]undec-7-ene (DBU); Dicyclohexylphosphino-2',4',6'-triisopropylbiphenyl (X-Phos); N,N-diisopropylethylamine (DIPEA, DIEA or Hunig's base); N;N-dimethylformamide (DMF); dimethylsulfide (DMS); dioxane is 1,4-dioxane; 1,2-dichloroethane (DCE); 1-chloroethylchloroformate (ACE-Cl); 1,1'-bis(diphenylphosphino)ferrocene (dppf, DPPF); ethyl acetate (EtOAc or EA); diethyl ether (ether or Et$_2$O); petroleum ether (PE or petrol ether); gram(s) (g); hexane (Hex); hour(s) (h or hr); hexamethylphosphoramide (HMPA); high pressure liquid chromatography (HPLC); 2-propanol (IPA); lithium diisopropylamide (LDA); mass spectrum (ms or MS); methanol-d4 (CD$_3$OD); microliter(s) (µL); milligram(s) (mg); milliliter(s) (mL); millimole (mmol); minute(s) (min); methyl t-butylether (MTBE); medium pressure liquid chromatography (MPLC); N-methylmorpholine-N-oxide (NMO); Pd(dppf)Cl$_2$ or PdCl$_2$ (dppf) is 1,1'-Bis(diphenylphosphino)ferrocene]dichloropalladium(II) which may be complexed with CH$_2$Cl$_2$; phenyl (Ph); potassium bis(trimethylsilyl)amide (KHMDS); p-toluenesulfonic acid (TsOH or PTSA); tetrakis(triphenylphosphine)palladium (Pd(PPh$_3$)$_4$); tris(dibenzylidineacetone)dipalladium (Pd$_2$(dba)$_3$); retention time (R$_t$); room temperature (rt or RT); saturated (sat. or sat'd); saturated aqueous sodium chloride solution (brine); sodium triacetoxyborohydride (NaBH(OAc)$_3$); trifluoromethanesulfonic anhydride (triflic anhydride, (Tf)$_2$O); triethylamine (TEA); trifluoroacetic acid (TFA); tetrahydrofuran (THF); flash chromatography (FC); liquid chromatography (LC); liquid chromatography-mass spectrometry (LCMS, LC/MS or LC-MS); supercritical fluid chromatography (SFC); t-butyloxycarbonyl (Boc or BOC); Diethylaminosulfur trifluoride (DAST); Diethylaminodifluorosulfinium tetrafluoroborate (XtalFluor-E); dichloromethane (DCM); dimethylacetamide (DMA; DMAC); dimethylsulfoxide (DMSO); 1,3-Bis(diphenylphosphino) propane (DPPP); 4,5-Bis(diphenylphosphino)-9,9-dimethylxanthene (Xantphos); acetic acid (HOAc); methyl (Me); methanol (MeOH); N-bromosuccinimide (NBS); N-chlorosuccinimide (NCS); N-iodosuccinimide (NIS); thin layer chromatography (TLC). CELITE® is a trademark name for diatomaceous earth, and SOLKA FLOC® is a trademark name for powdered cellulose. X or x may be used to express the number of times an action was repeated (e.g., washed with 2×200 mL 1N HCl), or to convey a dimension (e.g., the dimension of a column is 30×250 mm).

The following are representative procedures for the preparation of intermediates used to prepare the final products described in the Examples that follow thereafter. These examples are provided for the purpose of further illustration only and are not intended to be limitations on the disclosed invention.

It is understood that a chiral center in a compound may exist in the "S" or "R" stereo-configurations, or as a mixture of both. In many of the examples for intermediate compounds and final compounds, such compounds having a racemic chiral center were separated into individual stereoisomers, for example, referred to as isomer A (or enantiomer A or the like), which refers to the observed faster eluting isomer, and isomer B (or enantiomer B or the like), which refers to the observed slower eluting isomer, and each such isomer may be noted in the example as either the fast or slow eluting isomer. When a single "A" or "B" isomer intermediate is used to prepare a downstream compound, the downstream compound may take the "A" or "B" designation that corresponds to the previously used intermediate. Any Intermediates described below may be referred to herein by their number preceded by "I-" or "Int-." For illustration, in the example titled "Intermediate 3," the racemic parent title compound would be referred to as Intermediate 3 (or I-3), and the separated stereoisomers are noted as Intermediates 3A and 3B (or I-3A and I-3B). In some examples, compounds having a chiral center were derived synthetically from a single isomer intermediate; e.g., Example 4 was made using stereoisomer I-9B. Except for a defined chiral center in a parent isomer mixture, absolute stereochemistry (R or S) of each of the separated isomers was not determined, unless specifically described otherwise. An asterisk (*) may be used in a chemical structure drawing that indicates the location of a chiral center.

INTERMEDIATE 1

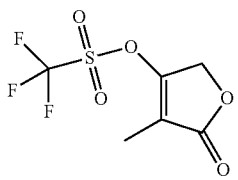

4-Methyl-5-oxo-2,5-dihydrofuran-3-yl trifluoromethanesulfonate

Step A: Ethyl 4-bromo-2-methyl-3-oxobutanoate

To a solution of ethyl 2-methyl-3-oxobutanoate (5.05 g, 35.0 mmol) in water (10 mL) at 0° C. was added bromine (1.805 mL, 35.0 mmol) dropwise over 2 h. The resulting mixture was stirred at room temperature for 16 h, and extracted with ethyl acetate. The organic layer was separated, dried over sodium sulfate, and concentrated in vacuum to give the title compound. $^1$H NMR (500 MHz, CDCl$_3$), δ 4.32-4.27 (m, 2H), 2.455 (s, 2H), 1.99 (s, 3H), 1.337-1.31 (t, 3H).

Step B: 4-Hydroxy-3-methylfuran-2(5H)-one

A mixture of ethyl 4-bromo-2-methyl-3-oxobutanoate (7.81 g, 35 mmol) and hydrogen bromide (0.040 mL, 48%, 0.35 mmol) was heated at 100° C. for 6 h. The precipitate was collected by filtration, and washed with ethyl acetate to give the title compound. $^1$H NMR (500 MHz, CDCl$_3$), δ 4.60 (s, 2H), 3.31 (s, 1H), 1.69 (s, 3H).

Step C: 4-Methyl-5-oxo-2,5-dihydrofuran-3-yl trifluoromethanesulfonate

To a solution of 4-hydroxy-3-methylfuran-2(5H)-one (400 mg, 3.51 mmol) in dichloromethane (10 mL) at −78° C. were added 2,6-lutidine (0.612 mL, 5.26 mmol) and trifluoromethanesulfonic anhydride (0.711 mL, 4.21 mmol) dropwise. The reaction mixture was stirred at −78° C. for 0.5 h, and at rt for 1 h. The mixture was diluted with dichloromethane, washed with 1 N hydrogen chloride three times and saturated sodium bicarbonate solution, dried over sodium sulfate, and concentrated under reduced pressure to give the title compound. LCMS [M+1]$^+$=247.0.

INTERMEDIATE 2

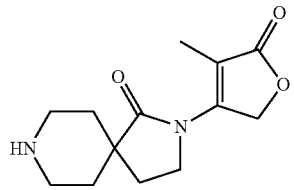 [SMILES: CC1=C(N2CCC3(CCNCC3)C2=O)COC1=O]

2-(4-Methyl-5-oxo-2,5-dihydrofuran-3-yl)-2,8-diazaspiro[4.5]decan-1-one

Step A: Methyl piperidine-4-carboxylate

To a solution of piperidine-4-carboxylic acid (1000 g, 7.75 mol) in MeOH (8000 mL) was added SOCl$_2$ (1000 mL) at 0° C. The mixture was stirred at rt for 18 h and concentrated to give the title compound. $^1$H-NMR (400 MHz, CD$_3$OD) δ 3.74 (s, 3H), 3.43-3.35 (m, 2H), 3.12-3.06 (m, 2H), 2.81-2.74 (m, 1H), 2.20-2.15 (m, 2H), 1.95-1.85 (m, 2H).

Step B: 1-tert-Butyl 4-methyl piperidine-1,4-dicarboxylate

To a solution of methyl piperidine-4-carboxylate (1400 g, 7.75 mol) in DCM (8000 mL) were added NaHCO$_3$ (1953 g, 23.21 mol) and Boc$_2$O (2030 g, 9.3 mol) dropwise at 0° C. The mixture was stirred at rt for 18 h, and was filtered. The filtrate was concentrated in vacuum to give the title compound. $^1$H-NMR (400 MHz, CDCl$_3$) δ 4.100-3.90 (m, 2H), 3.68 (s, 3H), 2.85-2.79 (m, 2H), 2.47-2.41 (m, 1H), 1.88-1.80 (m, 2H), 1.66-1.52 (m, 2H), 1.47 (s, 9H).

Step C: 1-tert-Butyl 4-methyl 4-(cyanomethyl)piperidine-1,4-dicarboxylate

To a solution of 1-tert-butyl 4-methyl piperidine-1,4-dicarboxylate (185 g, 761.3 mmol) in THF (1200 mL) was added dropwise of LDA [prepared from n-BuLi (2.5 M, 420 mL) and diisopropylamine (128 g, 1.07 mol) in THF (300 mL)] at −70° C. under N$_2$. The mixture was stirred at −70° C. for 1.5 h, and to this mixture was added a solution of bromoacetonitrile (128 g, 1.12 mol) in THF (300 mL) at −70° C. Stirring continued at −70° C. for 1 h and at 20° C. for 18 h. The resulting mixture was quenched with H$_2$O. The organic layer was separated, and the aqueous was extracted with EtOAc three times. The combined organic extracts were dried over Na$_2$SO$_4$ and concentrated. The residue was purified by silica gel chromatography eluted with PE/EA (5:1) to give the title compound. $^1$H-NMR (400 MHz, CDCl$_3$) δ 3.90-3.75 (m, 5H), 3.12-3.00 (m, 2H), 2.61-2.56 (m, 2H), 2.19-2.1 (m, 2H), 1.59-1.50 (m, 2H), 1.40 (s, 9H).

Step D: tert-Butyl 1-oxo-2,8-diazaspiro[4.5]decane-8-carboxylate

To a solution of 1-tert-butyl 4-methyl 4-(cyanomethyl)piperidine-1,4-dicarboxylate (350 g, 1.2 mol) in MeOH (6000 mL) were added NH₃.H₂O (400 mL) and Raney-Ni (300 g) at rt. The mixture was stirred under 2 MPa of hydrogen at 50° C. for 18 h, and filtered. The filtrate was concentrated. The crude product was washed with EtOAc to give the title compound. ¹H-NMR (400 MHz, CDCl₃) δ 6.30 (s, 1H), 4.08-3.92 (m, 2H), 3.38-3.30 (m, 2H), 3.01-2.91 (m, 2H), 2.10-2.00 (m, 2H), 1.88-1.78 (m, 2H), 1.49-1.32 (m, 11H).

Step E: tert-Butyl 2-(4-methyl-5-oxo-2,5-dihydro-furan-3-yl)-1-oxo-2,8-diazaspiro[4.5]decane-8-carboxylate To a mixture of tert-butyl 1-oxo-2,8-diazaspiro[4.5]decane-8-carboxylate (80.0 g, 315 mmol) and 4-methyl-5-oxo-2,5-dihydrofuran-3-yl trifluoromethanesulfonate (Int. 1; 85.2 g, 346 mmol), Xantphos (13.6 g, 23.6 mmol), and Cs₂CO₃ (153.7 g, 471.8 mmol) in toluene (1200 mL), was added Pd₂(dba)₃ (7.20 g, 7.86 mmol) under N₂. The reaction mixture was heated at 90° C. under N₂ for 18 h, filtered through a pad of CELITE. The filtrate was concentrated. The residue was purified via crystallization to give the title compound. ¹H NMR (400 MHz, CDCl₃) δ 5.23 (s, 2H), 4.02-3.99 (m, 4H), 3.06-3.05 (m, 2H), 2.15-2.11 (m, 2H), 2.02 (s, 3H), 1.87-1.81 (m, 2H), 1.51-1.41 (m, 11H).

Step F: 2-(4-Methyl-5-oxo-2,5-dihydrofuran-3-yl)-2,8-diazaspiro[4.5]decan-1-one

To a mixture of tert-butyl 2-(4-methyl-5-oxo-2,5-dihydrofuran-3-yl)-1-oxo-2,8-diazaspiro[4.5]decane-8-carboxylate (57.0 g, 163 mmol) in EtOAc (180 mL) was added saturated HCl(g)/EtOAc (712 mL) at 0° C. The reaction mixture was stirred at room temperature for 3 h, and filtered. The filtrate was concentrated to give the HCl salt. To a mixture of HCl salt (54.2 g, 189 mmol) in MeOH (550 mL) was added NaHCO₃ (31.8 g, 378 mmol) at ° C. The mixture was stirred at rt for 3 h until the pH=8. The mixture was filtered, and the filtrate was concentrated. The residue was re-dissolved in MeOH, and concentrated until a precipitate appeared. The precipitate was filtered off. The filtrate was concentrated to give the title compound as a free amine. 1H NMR (400 MHz, CD₃OD) δ 5.24 (s, 2H), 4.10-4.07 (m, 2H), 3.22-3.16 (m, 2H), 2.93-2.87 (m, 2H), 2.22-2.19 (m, 2H), 2.0 (s, 3H), 1.94-1.87 (m, 2H), 1.67-1.61 (m, 2H).

INTERMEDIATE 3A

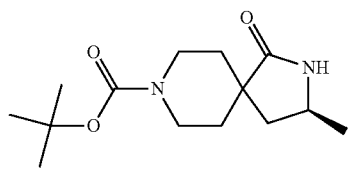 [SMILES: C[C@H]1CC2(CCN(C(=O)OC(C)(C)C)CC2)C(=O)N1]

(S)-tert-Butyl 3-methyl-1-oxo-2,8-diazaspiro[4.5]decane-8-carboxylate

INTERMEDIATE 3B

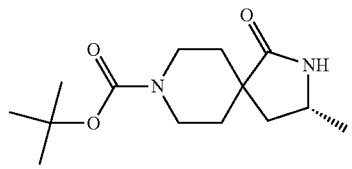 [SMILES: C[C@@H]1CC2(CCN(C(=O)OC(C)(C)C)CC2)C(=O)N1]

(R)-tert-Butyl 3-methyl-1-oxo-2,8-diazaspiro[4.5]decane-8-carboxylate

Step A: 1-tert-Butyl 4-methyl 4-(2-methylallyl)piperidine-1,4-dicarboxylate

A solution of N-boc-piperidine-4-carboxylic acid methyl ester (2 g, 8.22 mmol) in THF (40 ml) was cooled to −78° C. Under nitrogen, to this solution was added LDA (6.17 ml, 12.33 mmol, 2.0 M in THF) dropwise. The reaction mixture was stirred at −78° C. for 30 minutes, and a solution of 3-bromo-2-methylpropene (1.6 g, 11.85 mmol) in THF (2 ml) was added. After the mixture was stirred for 1 h at the same temperature, the reaction was quenched with saturated ammonium chloride aqueous (5 ml). The mixture was allowed to warm up to rt, extracted with EtOAc twice. The combined organic layers were washed with brine, dried over anhydrous sodium sulfate and filtered. The filtrate was concentrated and the crude product was purified by silica gel column chromatography eluting with 0-30% ethyl acetate/hexane to give the title compound. LCMS [M−56+1]⁺ =242.2.

Step B: 1-tert-Butyl 4-methyl 4-(2-oxopropyl)piperidine-1,4-dicarboxylate

To a solution of 1-tert-butyl 4-methyl 4-(2-methylallyl)piperidine-1,4-dicarboxylate (2.2 g, 7.40 mmol) in dioxane/water (60 ml, 1/1) under nitrogen was added osmium tetraoxide (0.038 g, 0.148 mmol) and sodium periodate (2.88 g, 13.46 mmol). The mixture was stirred at rt for 3 h. The mixture was then diluted with dichloromethane, and washed with 20% Na₂S₂O₃ (20 ml). The organic layers were combined and washed with brine, dried over anhydrous sodium sulfate, and filtered. The filtrates were concentrated and the residue was purified by silica gel column chromatography eluting with 0-60% ethyl acetate in hexane to afford the title compound. LCMS [M+23]⁺=322.2.

Step C: tert-Butyl 3-methyl-1-oxo-2,8-diazaspiro[4.5]decane-8-carboxylate (racemic)

To a solution of 1-tert-butyl 4-methyl 4-(2-oxopropyl)piperidine-1,4-dicarboxylate (1.15 g, 3.84 mmol) in methanol (25 ml) were added ammonium acetate (3.85 g, 49.9 mmol), sodium cyanoborohydride (0.681 g, 10.83 mmol) and magnesium sulfate (2.54 g, 21.13 mmol). The mixture was heated at 80° C. in a sealed tube for 12 hours, cooled to rt, and filtered through a pad of CELITE. The filter cake was washed with methanol. The combined filtrates were then concentrated, and the residue was purified by silica gel column chromatography eluting with 0-10% methanol in ethyl acetate to afford the title compound. LCMS [M+23]⁺=291.2.

Step D: (S)-tert-Butyl 3-methyl-1-oxo-2,8-diazaspiro[4.5]decane-8-carboxylate, and (R)-tert-Butyl 3-methyl-1-oxo-2,8-diazaspiro[4.5]decane-8-carboxylate tert-Butyl 3-methyl-1-oxo-2,8-diazaspiro[4.5]decane-8-carboxylate (racemic) was subjected to SFC chiral separation. The two enantiomers were resolved on CHIRALCEL IA column eluting with 30% MeOH:MeCN (2:1)/CO₂ (10 MPa, 35° C.). The fast eluting component was (S)-tert-Butyl 3-methyl-1-oxo-2,8-diazaspiro[4.5]decane-8-carboxylate, and the slow eluting component was (R)-tert-Butyl 3-methyl-1-oxo-2,8-diazaspiro[4.5]decane-8-carboxylate.

INTERMEDIATE 4A

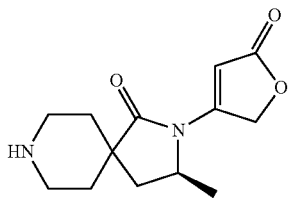 [SMILES: C[C@H]1CC2(CCNCC2)C(=O)N1C1=CC(=O)OC1]

(S)-3-methyl-2-(5-oxo-2,5-dihydrofuran-3-yl)-2,8-diazaspiro[4.5]decan-1-one

Step A: (S)-tert-butyl 3-methyl-1-oxo-2-(5-oxo-2,5-dihydrofuran-3-yl)-2,8-diazaspiro[4.5]decane-8-carboxylate To a sealed tube was added (S)-tert-butyl 3-methyl-1-oxo-2,8-diazaspiro[4.5]decane-8-carboxylate (Int. 3A; 4.20 g, 15.65 mmol), 4-bromofuran-2-one (3.83 g, 23.48 mmol), 4,5-bis(diphenylphosphino)-9,9-dimethylxanthene (3.62 g, 6.26 mmol), $K_2CO_3$ (4.33 g, 31.3 mmol), water (846 µl, 47.0 mmol) and palladium (II) acetate (0.376 g, 1.675 mmol) and toluene (80 ml). The resulting mixture was bubbled with $N_2$ gas for 20 min. The tube was sealed and the mixture was heated at 90° C. for 48 hrs. After cooling to rt, the mixture was diluted with EtOAc and filtered. The filtrates were concentrated and the residue was purified by silica gel column chromatography using 0-100% EtOAc/hexane as the gradient to give the title compound. LCMS$[M+1]^+$=351.4.

Step B: (S)-3-methyl-2-(5-oxo-2,5-dihydrofuran-3-yl)-2,8-diazaspiro[4.5]decan-1-one To the solution of (S)-tert-butyl 3-methyl-1-oxo-2-(5-oxo-2,5-dihydrofuran-3-yl)-2,8-diazaspiro[4.5]decane-8-carboxylate (1.78 g, 5.08 mmol) in DCM (20 mL) was added trifluoroacetic acid (10 ml). The resulting solution was stirred at rt for 1 hr. The solution was concentrated and the residue was basified on ion-exchange column (SCX) by washing with methanol and eluting with 1 N ammonia/methanol to give the title compound. LCMS $[M+1]^+$=251.23.

INTERMEDIATE 4B

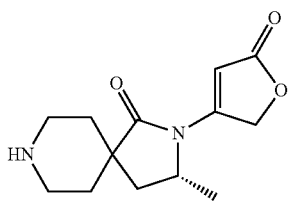 [SMILES: C[C@@H]1CC2(CCNCC2)C(=O)N1C1=CC(=O)OC1]

(R)-3-methyl-2-(5-oxo-2,5-dihydrofuran-3-yl)-2,8-diazaspiro[4.5]decan-1-one (R)-3-methyl-2-(5-oxo-2,5-dihydrofuran-3-yl)-2,8-diazaspiro[4.5]decan-1-one was prepared using a similar procedure as (S)-3-methyl-2-(5-oxo-2,5-dihydrofuran-3-yl)-2,8-diazaspiro[4.5]decan-1-one (intermediate 4A), but starting in step (A) with (R)-tert-butyl 3-methyl-1-oxo-2,8-diazaspiro[4.5]decane-8-carboxylate (Int. 3B).

INTERMEDIATE 5

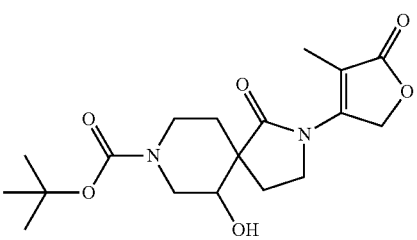 [SMILES: CC1=C(N2CCC3(CCN(C(=O)OC(C)(C)C)CC3O)C2=O)COC1=O]

tert-butyl 6-hydroxy-2-(4-methyl-5-oxo-2,5-dihydrofuran-3-yl)-1-oxo-2,8-diazaspiro[4.5]decane-8-carboxylate (cis)

Step A: Ethyl 1-benzyl-4-(cyanomethyl)-3-oxopiperidine-4-carboxylate

To a flask charged with ethyl 1-benzyl-3-oxopiperidine-4-carboxylate (1.0 g, 3.8 mmol) and a stir bar was added $K_2CO_3$ (1.06 g, 7.6 mmol), bromoacetonitrile (0.92 g, 7.6 mmol), and acetone (15 mL). The reaction was allowed to stir at rt for 2 h, then heated to 45° C. for 3 h. The reaction was quenched with saturated $NH_4Cl$ solution, extracted with EtOAc, dried over $Na_2SO_4$, filtered and concentrated. The crude product was purified by MPLC using 10-100% acetonitrile (0.1% TFA)/water (0.1% TFA) as the gradient to furnish the title compound. LCMS $[M+1]^+$=301.

Step B: 8-Benzyl-6-hydroxy-2,8-diazaspiro[4.5]decan-1-one

To a flask charged with ethyl 1-benzyl-4-(cyanomethyl)-3-oxopiperidine-4-carboxylate (900 mg, 3.0 mmol) were added platinum oxide (100 mg, 0.44 mmol), MeOH (20 mL) and acetic acid (20 mL). The mixture was allowed to stir vigorously under an atmosphere of hydrogen for 24 h. The catalyst was removed by filtration through a pad of CELITE, and the filtrate was concentrated under reduced pressure. The residue was dissolved in EtOH (100 mL), and $K_2CO_3$ (2.1 g, 15 mmol) was added. The mixture was heated at 90° C. for 4 h, cooled to rt, and DCM (200 mL) was added to precipitate the solids. The solids were then removed by filtration, the filtrate was concentrated, and the residue was purified on a silica gel column using 0-10% MeOH/DCM (mixed with 10% $NH_4OH$) as eluting solvents to give the title compound. LCMS $[M+1]^+$=261.

Step C: 8-Benzyl-6-hydroxy-2-(4-methyl-5-oxo-2,5-dihydrofuran-3-yl)-2,8-diazaspiro[4.5]decan-1-one (trans and cis)

To a flask charged with 8-benzyl-6-hydroxy-2,8-diazaspiro[4.5]decan-1-one (520 mg, 2.0 mmol) were added palladium acetate (22 mg, 0.10 mmol), $K_2CO_3$ (550 mg, 4.00 mmol), Xantphos (120 mg, 0.20 mmol), 4-Methyl-5-oxo-2,5-dihydrofuran-3-yl trifluoromethanesulfonate (Int. 1; 640 mg, 2.6 mmol), and water (110 mg, 6.0 mmol). The mixture was heated to 60° C. for 16 h. The reaction mixture was diluted with EtOAc, washed with water, dried over $Na_2SO_4$, filtered and concentrated. The resultant oil was loaded onto a silica gel column, and eluted with EtOAc/ hexane. Two peaks were separated. The fast eluting peak was the minor product (Bn-trans, racemic), and the slow moving spot was the major product (Bn-cis, racemic). LCMS [M+1]⁺=357.

Step D: tert-Butyl 6-hydroxy-2-(4-methyl-5-oxo-2,5-dihydrofuran-3-yl)-1-oxo-2,8-diazaspiro[4.5]decane-8-carboxylate (cis)

To a solution of 8-benzyl-6-hydroxy-2-(4-methyl-5-oxo-2,5-dihydrofuran-3-yl)-2,8-diazaspiro[4.5]decan-1-one (cis) (10 g, 28.2 mmol) and di-tert-butylcarbonate (7.21 ml, 31.0 mmol) in methanol (50 ml) was added palladium on carbon (1.501 g, 1.411 mmol). The resulting mixture was subjected to hydrogenation at 45 Psi at rt over the weekend, and filtered through CELITE under nitrogen. The filtrate was concentrated and the residue was purified on silica gel using ethyl acetate/hexane as eluting solvents to give the title compound. LCMS [M+1]⁺=367.1.

Step E: tert-Butyl 6-hydroxy-2-(4-methyl-5-oxo-2,5-dihydrofuran-3-yl)-1-oxo-2,8-diazaspiro[4.5]decane-8-carboxylate (trans)

tert-Butyl 6-hydroxy-2-(4-methyl-5-oxo-2,5-dihydrofuran-3-yl)-1-oxo-2,8-diazaspiro[4.5]decane-8-carboxylate (trans) was synthesized following a similar procedure to that for tert-Butyl 6-hydroxy-2-(4-methyl-5-oxo-2,5-dihydrofuran-3-yl)-1-oxo-2,8-diazaspiro[4.5]decane-8-carboxylate (cis) started with 8-benzyl-6-hydroxy-2-(4-methyl-5-oxo-2,5-dihydrofuran-3-yl)-2,8-diazaspiro[4.5]decan-1-one (trans). LCMS [M+1]⁺=367.1.

INTERMEDIATE 6A

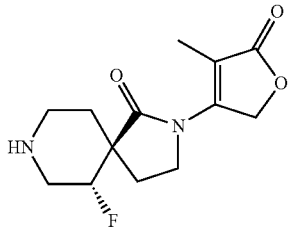 [SMILES: CC1=C(N2CC[C@]3(CCNC[C@H]3F)C2=O)COC1=O]

(5R,6S)-6-fluoro-2-(4-methyl-5-oxo-2,5-dihydrofuran-3-yl)-2,8-diazaspiro[4.5]decan-1-one (trans, enantiomer A)

Step A: (5S,6S)-tert-butyl 6-fluoro-2-(4-methyl-5-oxo-2,5-dihydrofuran-3-yl)-1-oxo-2,8-diazaspiro[4.5]decane-8-carboxylate (trans, fast enantiomer A) and (5R,6R)-tert-butyl 6-fluoro-2-(4-methyl-5-oxo-2,5-dihydrofuran-3-yl)-1-oxo-2,8-diazaspiro[4.5]decane-8-carboxylate (trans, slow, enantiomer B)

To the solution of tert-butyl 6-hydroxy-2-(4-methyl-5-oxo-2,5-dihydrofuran-3-yl)-1-oxo-2,8-diazaspiro[4.5]decane-8-carboxylate (intermediate 5, cis, racemic) (1.84 g, 5.02 mmol) in methylene chloride (100 ml) was added DAST (0.863 ml, 6.53 mmol) dropwise under nitrogen at 0° C. The resulting solution was stirred at 0° C. for 2.5 h, and quenched with addition of 200 mL saturated sodium bicarbonate. The organic layer was separated, and the aqueous layer was extracted with methylene chloride two times. The combined organic layers were dried over sodium sulfate, concentrated and the residue was purified on silica gel column using ethyl acetate/hexane as eluting solvents to give tert-butyl 6-fluoro-2-(4-methyl-5-oxo-2,5-dihydrofuran-3-yl)-1-oxo-2,8-diazaspiro[4.5]decane-8-carboxylate (trans, racemic). LCMS [M+1]⁺=369.19. The racemate was separated on chiral AD-H column using methanol (0.05% DEA) in CO₂ to give (5S,6S)-tert-butyl 6-fluoro-2-(4-methyl-5-oxo-2,5-dihydrofuran-3-yl)-1-oxo-2,8-diazaspiro[4.5]decane-8-carboxylate (trans, fast enantiomer A), and (5R,6R)-tert-butyl 6-fluoro-2-(4-methyl-5-oxo-2,5-dihydrofuran-3-yl)-1-oxo-2,8-diazaspiro[4.5]decane-8-carboxylate (trans, slow, enantiomer B). LCMS [M+1−56]⁺=313.0.

Step B: (5R,6S)-6-fluoro-2-(4-methyl-5-oxo-2,5-dihydrofuran-3-yl)-2,8-diazaspiro[4.5]decan-1-one (trans, enantiomer A)

To a solution of (5S,6S)-tert-butyl 6-fluoro-2-(4-methyl-5-oxo-2,5-dihydrofuran-3-yl)-1-oxo-2,8-diazaspiro[4.5]decane-8-carboxylate (trans, fast enantiomer A) (0.60 g, 1.629 mmol) in methylene chloride (5 ml) was added trifluoroacetic acid (5 ml, 64.9 mmol). The resulting solution was stirred at rt for 2 h, and concentrated. The residue was basified on BOND ELUT SCX ion exchange column washed with MeOH to remove the acid followed by eluting with 1 N ammonia in methanol to give (5R,6S)-6-fluoro-2-(4-methyl-5-oxo-2,5-dihydrofuran-3-yl)-2,8-diazaspiro[4.5]decan-1-one (trans, enantiomer A). LCMS [M+1]⁺=269.0.

INTERMEDIATE 6B

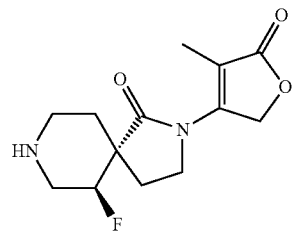 [SMILES: CC1=C(N2CC[C@@]3(CCNC[C@@H]3F)C2=O)COC1=O]

(5S,6R)-6-fluoro-2-(4-methyl-5-oxo-2,5-dihydrofuran-3-yl)-2,8-diazaspiro[4.5]decan-1-one (trans, enantiomer B)

To a solution of (5R,6R)-tert-butyl 6-fluoro-2-(4-methyl-5-oxo-2,5-dihydrofuran-3-yl)-1-oxo-2,8-diazaspiro[4.5]decane-8-carboxylate (Int. 6A, step A, trans, slow, enantiomer B) (0.60 g, 1.629 mmol) in methylene chloride (5 ml) was added trifluoroacetic acid (5 ml, 64.9 mmol). The resulting solution was stirred at rt for 2 h, and concentrated. The residue was basified on BOND ELUT SCX ion exchange column, washed with MeOH to remove the acid and then eluted with 1 N ammonia in methanol to give (5S,6R)-6-fluoro-2-(4-methyl-5-oxo-2,5-dihydrofuran-3-yl)-2,8-diazaspiro[4.5]decan-1-one (trans, enantiomer B). LCMS [M+1]⁺=269.0.

INTERMEDIATE 7

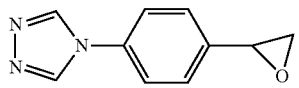 [SMILES: c1cc(-n2cnnc2)ccc1C1CO1]

4-(4-(oxiran-2-yl)phenyl)-4H-1,2,4-triazole

Step A: 4-(4-bromophenyl)-4H-1,2,4-triazole

A mixture of 4-bromoaniline (7.81 ml, 68.1 mmol) and 1,2-diformylhydrazine (6 g, 68.1 mmol) was heated at 180° C. for 3 h. After cooling to rt, the residue was purified by silica gel chromatography using 50-100% ethyl acetate/hexane as the eluting solvents to give the title compound. LC/MS [M+1]$^+$=223.90, 225.90.

Step B: 4-(4-vinylphenyl)-4H-1,2,4-triazole

A mixture of 4-(4-bromophenyl)-4H-1,2,4-triazole (7.85 g, 35.0 mmol), PdCl$_2$ (dppf)-CH$_2$Cl$_2$ adduct (1.431 g, 1.752 mmol), triethylamine (9.77 ml, 70.1 mmol), and potassium vinyltrifluoroborate (9.39 g, 70.1 mmol) in ethanol (100 ml) was heated at reflux for 4 h under N$_2$. After filtration through CELITE, the filtrate was concentrated and the residue was purified on silica gel column using ethyl acetate as the eluting solvent to give the title compound. LC/MS [M+1]$^+$=172.01.

Step C: 4-(4-(oxiran-2-yl)phenyl)-4H-1,2,4-triazole

To a solution of 4-(4-vinylphenyl)-4H-1,2,4-triazole (100 mg, 0.584 mmol) in methylene chloride (1 ml) was added mCPBA (196 mg, 0.876 mmol) and the resulting solution was stirred at rt overnight. The solution was partitioned between 10% potassium carbonate (50 ML) and methylene chloride (50 mL). The alkaline phase was extracted with methylene chloride twice, the combined organic phase wa dried over sodium sulphate, concentrated and the residue was purified on TLC using ethyl acetate as the developing solvent to give the title compound. LC/MS [M+1]$^+$=188.03. $^1$HNMR (500 MHz, CDCl$_3$), δ 8.479 (s, 2H), 7.454-7.384 (m, 4H), 3.925 (br s, 1H), 3.204-3.186 (m, 1H), 2.783-2.777 (m, 1H).

INTERMEDIATE 8

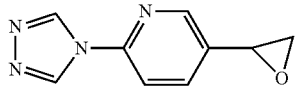 [SMILES: c1cc(-n2cnnc2)ncc1C1CO1]

5-(oxiran-2-yl)-2-(4H-1,2,4-triazol-4-yl)pyridine

Step A: 5-bromo-2-(4H-1,2,4-triazol-4-yl)pyridine

A mixture of 5-bromopyridin-2-amine (9.43 g, 54.5 mmol) and 1,2-diformylhydrazine (4.8 g, 54.5 mmol) was heated at 190° C. for 1.5 h. After cooling to rt, the residue was treated with DCM, the solid was collected by filtration, and washed with DCM to give the title compound. LC/MS [M+1]$^+$=224.93, 226.93.

Step B: 2-(4H-1,2,4-triazol-4-yl)-5-vinylpyridine

A mixture of 5-bromo-2-(4H-1,2,4-triazol-4-yl)pyridine (3.4 g, 15.11 mmol), PdCl$_2$ (dppf)-CH$_2$Cl$_2$ adduct (0.617 g, 0.755 mmol), triethylamine (4.21 ml, 30.2 mmol) and potassium vinyltrifluoroborate (4.05 g, 30.2 mmol) in ethanol (50 ml)) was heated at reflux for 3 h under N$_2$. After filtration through CELITE, the filtrate was concentrated and the residue was purified on silica gel column using ethyl acetate as the eluting solvent to give the title compound. LC/MS [M+1]$^+$=173.11.

Step C: 5-(oxiran-2-yl)-2-(4H-1,2,4-triazol-4-yl)pyridine

To a suspension of 2-(4H-1,2,4-triazol-4-yl)-5-vinylpyridine (1.45 g, 8.42 mmol) in tert-butanol (50 ml) and water (50.0 ml) was added NBS (1.499 g, 8.42 mmol) and the resulting suspension was heated at 40° C. overnight. After cooling to 0° C., NaOH (1.010 g, 25.3 mmol) in 5 mL water was added dropwise, and the resulting solution was stirred at 0° C. for 2 h. The reaction mixture was extracted with DCM twice. The combined organic phase was dried over Na$_2$SO$_4$, concentrated and the residue was purified on silica gel column using 0-10% MeOH/DCM as eluting solvents to give the title compound. LC/MS [M+1]$^+$=189.12.

INTERMEDIATE 9A

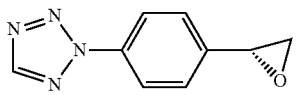 [SMILES: c1nnn(-c2ccc([C@@H]3CO3)cc2)n1]

(R)-2-(4-(oxiran-2-yl)phenyl)-2H-tetrazole

INTERMEDIATE 9B

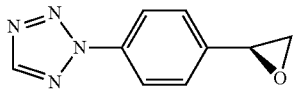

(S)-2-(4-(oxiran-2-yl)phenyl)-2H-tetrazole

Step A: 4-(2H-tetrazol-2-yl)phenyl trifluoromethanesulfonate

To a solution of 4-(2H-tetrazol-2-yl)phenol (2.5 g, 15.42 mmol) in DCM (80 ml) was added N-ethyl-N-isopropylpropan-2-amine (4.04 ml, 23.13 mmol), and the solution was cooled to −5° C. Trifluoromethanesulfonic anhydride (3.13 ml, 18.50 mmol) was added dropwise to the above solution. The resulting solution was stirred at −5° C. for 20 min, then at 0° C. for 1 h. The reaction was quenched with sat. NaHCO$_3$, and partitioned between DCM and sat. NaHCO$_3$. The alkaline phase was extracted with DCM four times. The combined organic phase was dried over Na$_2$SO$_4$, and concentrated to give the title compound. LC/MS [M+1]$^+$=295.13.

Step B: 2-(4-vinylphenyl)-2H-tetrazole

A solution of potassium vinyltrifluoroborate (3.23 g, 24.13 mmol) and 4-(2H-tetrazol-2-yl)phenyl trifluoromethanesulfonate (3.55 g, 12.07 mmol) in ethanol (60 ml) was flushed with N$_2$ for 30 min followed by addition of PdCl$_2$ (dppf)-CH$_2$Cl$_2$ adduct (0.493 g, 0.603 mmol) and triethylamine (3.36 ml, 24.13 mmol). The resulting mixture was heated at reflux for 4.5 h under N$_2$. After filtration, the filtrate was concentrated and the residue was purified on a silica gel column using 20-70% EtOAc/hexane as eluting solvents to give the title compound. LC/MS [M+1]$^+$=173.2.

Step C: (R)-2-(4-(oxiran-2-yl)phenyl)-2H-tetrazole and (S)-2-(4-(oxiran-2-yl)phenyl)-2H-tetrazole To a suspension of 2-(4-vinylphenyl)-2H-tetrazole (1.78 g, 10.34 mmol) in tert-butanol (20 ml) and water (10.0 ml) was added NBS (1.840 g, 10.34 mmol) and the resulting suspension was stirred at rt for 2 h. After cooling to 0° C., a solution of sodium hydroxide (1.240 g, 31.0 mmol) in 5 mL water was added dropwise, the resulting solution was stirred at 0° C. for 2 h. The reaction mixture was extracted with DCM. The combined organic phase was dried over Na₂SO₄, concentrated and the residue was purified on silica gel column using 30-50% EtOAc/hexane as eluting solvents to give 2-(4-(oxiran-2-yl)phenyl)-2H-tetrazole as a racemate which was separated on CHIRALPAK AD-H column using 35% methanol/CO₂ as eluting solvents at 10 MPa to give the faster eluant (R)-2-(4-(oxiran-2-yl)phenyl)-2H-tetrazole, and the slower eluant (S)-2-(4-(oxiran-2-yl)phenyl)-2H-tetrazole. LC/MS [M+1]⁺=189.3.

EXAMPLE 1

(R)-8-(2-(4-(2H-tetrazol-2-yl)phenyl)-2-hydroxyethyl)-2-(4-methyl-5-oxo-2,5-dihydrofuran-3-yl)-2,8-diazaspiro[4.5]decan-1-one A mixture of 2-(4-methyl-5-oxo-2,5-dihydrofuran-3-yl)-2,8-diazaspiro[4.5]decan-1-one (Int. 2; 50 mg, 0.200 mmol) and (R)-2-(4-(oxiran-2-yl)phenyl)-2H-tetrazole (FAST) (Int. 9A) 48.9 mg, 0.260 mmol) in ethanol (3 ml) was heated at 95° C. overnight. After removing volatile liquid, the residue was purified on TLC using 30% MeOH/EtOAc as developing solvent to give a residue which was further purified on TLC using 10% MeOH/DCM as developing solvent to afford (R)-8-(2-(4-(2H-tetrazol-2-yl)phenyl)-2-hydroxyethyl)-2-(4-methyl-5-oxo-2,5-dihydrofuran-3-yl)-2,8-diazaspiro[4.5]decan-1-one. LC/MS [M+1]⁺=439.1, ¹H-NMR (500 Mz, CDCl₃), δ (ppm): 9.020 (s, 1H), 7.735-7.718 (d, J=8.5 Hz, 2H), 7.645-7.628 (d, J=8.3 Hz, 2H), 5.293 (s, 2H), 4.886-4.865 (m, 1H), 4.076-4.048 (t, J=6.8 Hz), 2H), 3.193-3.169 (m, 1H), 2.891-2.867 (m, 1H), 2.694-2.663 (m, 1H), 2.617-2.575 (t, J=10.5 Hz, 1H), 2.529-2.483 (m, 1H), 2.359-2.319 (t, J=10.0 Hz, 1H), 2.199-2.171 (t, J=7.0 Hz, 2H), 2.083 (s, 3H), 2.047-2.027 (m, 2H), 1.668-1.604 (t, J=6.2 Hz, 2H).

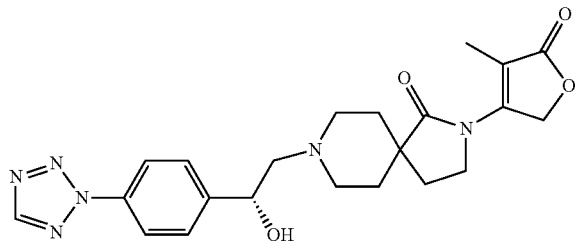 [SMILES: CC1=C(N2CCC3(CCN(C[C@H](O)c4ccc(-n5ncnn5)cc4)CC3)C2=O)COC1=O]

TABLE 1

Examples 2-6 were synthesized followed a similar procedure to that described in Example 1.

| Examples | Intermediates | Structures | Characterization |
|---|---|---|---|
| 2 | 7, 2 | 8-(2-(4-(4H-1,2,4-triazol-4-yl)phenyl)-2-hydroxyethyl)-2-(4-methyl-5-oxo-2,5-dihydrofuran-3-yl)-2,8-diazaspiro[4.5]decan-1-one (racemate) | LC/MS [M + 1]⁺ = 438.1 |
| 3 | 8, 2 | 8-(2-(6-(4H-1,2,4-triazol-4-yl)pyridin-3-yl)-2-hydroxyethyl)-2-(4-methyl-5-oxo-2,5-dihydrofuran-3-yl)-2,8-diazaspiro[4.5]decan-1-one (racemate) | LC/MS [M + 1]⁺ = 439.0 |
| 4 | 9B, 2 | (S)-8-(2-(4-(2H-tetrazol-2-yl)phenyl)-2-hydroxyethyl)-2-(4-methyl-5-oxo-2,5-dihydrofuran-3-yl)-2,8-diazaspiro[4.5]decan-1-one | LC/MS [M + 1]⁺ = 439.1 |

TABLE 1-continued

Examples 2-6 were synthesized followed a similar procedure to that described in Example 1.

| Examples | Intermediates | Structures | Characterization |
|---|---|---|---|
| 5 | 9B, 4A | (S)-8-((S)-2-(4-(2H-tetrazol-2-yl)phenyl)-2-hydroxyethyl)-3-methyl-2-(5-oxo-2,5-dihydrofuran-3-yl)-2,8-diazaspiro[4.5]decan-1-one | LC/MS [M + 1]⁺ = 439.1 |
| 6 | 9A, 4A | (S)-8-((R)-2-(4-(2H-tetrazol-2-yl)phenyl)-2-hydroxyethyl)-3-methyl-2-(5-oxo-2,5-dihydrofuran-3-yl)-2,8-diazaspiro[4.5]decan-1-one | LC/MS [M + 1]⁺ = 439.1 |

The following Thallium Flux Assay was performed on each of the final product compounds in the Examples.

Thallium Flux Assay

A Thallium Flux Assay was performed on the compounds of the Examples. This assay has been described previously; see, e.g., PCT Published Application WO 2013/062900.

Data collected for compounds in the Examples of the present invention using the Thallium Flux Assay are shown in Table 2 below. All of the tested final product compounds in the Examples (diastereomeric mixtures and individual diastereomers) had $IC_{50}$ potencies less than 1 μM in the Thallium Flux Assay.

TABLE 2

| Example No. | Thallium Flux $IC_{50}$ (μM) |
|---|---|
| 1 | 0.007 |
| 2 | 0.176 |
| 3 | 0.248 |
| 4 | 0.007 |
| 5 | 0.003 |
| 6 | 0.005 |

While the invention has been described with reference to certain particular embodiments thereof, numerous alternative embodiments will be apparent to those skilled in the art from the teachings described herein. The scope of the claims should not be limited by the preferred embodiments set forth in the examples, but should be given the broadest interpretation consistent with the description as a whole. Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. All patents, patent applications and publications cited herein are incorporated by reference in their entirety.

What is claimed is:

1. A compound having structural Formula I

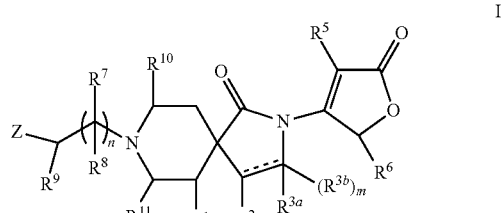

or a pharmaceutically acceptable salt thereof wherein:

Z is

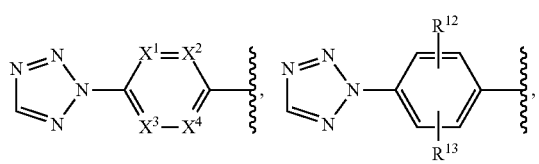

-continued

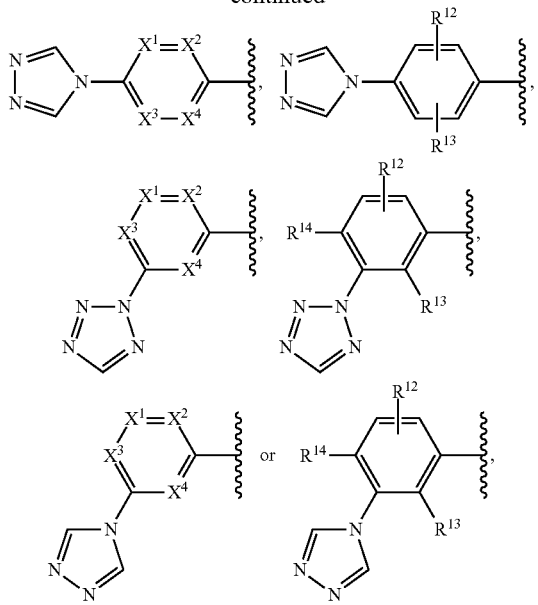

$X^1$, $X^2$, $X^3$ and $X^4$ are each independently selected from $C(R^4)$ and N, provided that at least one and at most two of $X^1$, $X^2$, $X^3$ and $X^4$ are N;
$R^1$ is —H, halo, —OH, or —$OC_{1-3}$alkyl;
$R^2$ is —H, =O, —OH, —$C_{1-3}$alkyl or —$OC_{1-3}$alkyl;
$R^{3a}$ is —H, —$C_{3-4}$cycloalkyl or —$C_{1-3}$alkyl optionally substituted with —$OCH_3$ or 1 to 3 of —F;
$R^{3b}$ is —H or —$C_{1-3}$alkyl, or $R^{3b}$ is absent when the dashed bond is a double bond;
or $R^{3a}$ and $R^{3b}$ are joined together with the carbon to which they are both attached to form cyclopropyl or cyclobutyl;
each $R^4$ is independently —H, halo, —CN, —$C_{3-6}$cycloalkyl, —$C(O)OC_{1-4}$alkyl, —$OC_{1-4}$alkyl, or —$C_{1-4}$alkyl optionally substituted with OH or 1-3 of —F;
$R^5$ is —H, halo, or —$C_{1-3}$alkyl optionally substituted with —O—$C_{1-3}$alkyl;
$R^6$ is —H or —$C_{1-3}$alkyl;
$R^7$ is —H or —$C_{1-3}$alkyl optionally substituted with —OH, —$OCH_3$ or 1 to 3 of —F, or $R^7$ is absent when n is zero;
$R^8$ is —H or —$C_{1-3}$alkyl, or $R^8$ is absent when n is zero;
or $R^7$ and $R^8$ are joined together with the carbon to which they are both attached to form cyclopropyl or cyclobutyl;
$R^9$ is —H, halo, —OH, —$C_{1-3}$alkyl, —$OC_{1-3}$alkyl or —$CH_2OH$;
$R^{10}$ is —H, or —$C_{1-3}$alkyl optionally substituted with —OH, —$OCH_3$, or 1 to 3 of —F;
$R^{11}$ is —H, or —$C_{1-3}$alkyl optionally substituted with —OH, —$OCH_3$, or 1 to 3 of —F;
or $R^{10}$ and $R^{11}$ are joined together to represent —$CH_2$—$CH_2$—, —$CH_2$—$N(CH_3)$—$CH_2$— or —$CH_2OCH_2$—;
$R^{12}$, $R^{13}$ and $R^{14}$ are each independently —H, halo, —CN, —$C_{3-6}$cycloalkyl, —$C(O)OC_{1-4}$alkyl, —$OC_{1-4}$alkyl, or —$C_{1-4}$alkyl optionally substituted with —OH or 1-3 of —F;
m is zero where $R^{3b}$ is absent, or one where $R^{3b}$ is present;
the partially dashed double bond ("(---)") represents a single or double bond wherein:
 (i) when m is one, then the dashed bond is a single bond; and
 (ii) when m is zero and $R^2$ is not =O, then the dashed bond is a double bond; and
n is zero or one.

2. The compound having structural Formula Ia

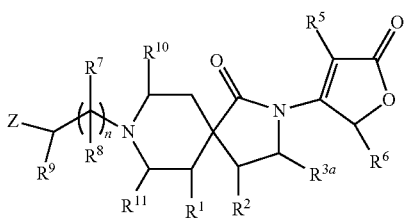

or a pharmaceutically acceptable salt thereof wherein:
Z is

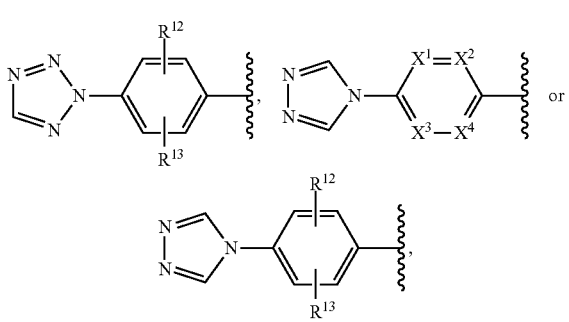

$X^1$, $X^2$, $X^3$ and $X^4$ are each independently selected from $C(R^4)$ and N, provided that at least one and at most two of $X^1$, $X^2$, $X^3$ and $X^4$ are N;
$R^1$ is —H, halo, —OH, or —$OC_{1-3}$alkyl;
$R^2$ is —H, =O, —OH, —$C_{1-3}$alkyl or —$OC_{1-3}$alkyl;
$R^{3a}$ is —H, —$C_{3-4}$cycloalkyl or —$C_{1-3}$alkyl optionally substituted with —$OCH_3$ or 1 to 3 of —F;
each $R^4$ is independently —H, halo, —CN, —$C_{3-6}$cycloalkyl, —$C(O)OC_{1-4}$alkyl, —$OC_{1-4}$alkyl, or —$C_{1-4}$alkyl optionally substituted with OH or 1-3 of —F;
$R^5$ is —H, halo, or —$C_{1-3}$alkyl optionally substituted with —O—$C_{1-3}$alkyl;
$R^6$ is —H or —$C_{1-3}$alkyl;
$R^7$ is —H or —$C_{1-3}$alkyl optionally substituted with —OH, —$OCH_3$ or 1 to 3 of —F, or $R^7$ is absent when n is zero;
$R^8$ is —H or —$C_{1-3}$alkyl, or $R^8$ is absent when n is zero;
$R^9$ is —H, halo, —OH, —$C_{1-3}$alkyl, —$OC_{1-3}$alkyl or —$CH_2OH$;
$R^{10}$ is —H, or —$C_{1-3}$alkyl optionally substituted with —OH, —$OCH_3$, or 1 to 3 of —F;
$R^{11}$ is —H, or —$C_{1-3}$alkyl optionally substituted with —OH, —$OCH_3$, or 1 to 3 of —F;
$R^{12}$ and $R^{13}$ are each independently —H, halo, —CN, —$C_{3-6}$cycloalkyl, —$C(O)OC_{1-4}$alkyl, —$OC_{1-4}$alkyl, or —$C_{1-4}$alkyl optionally substituted with —OH or 1-3 of —F; and
n is zero or one.
3. The compound of claim 1 wherein:
Z is

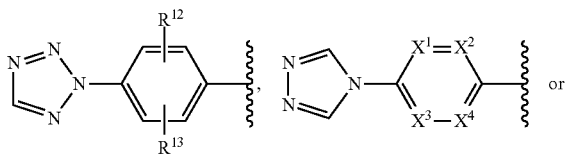

-continued

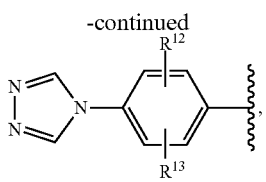

one of X¹ or X² is C(R⁴) and the other is N;
R¹ is —H, halo, —OH, or —OC$_{1-3}$alkyl;
R² is —H, =O, —OH, —C$_{1-3}$alkyl or —OC$_{1-3}$alkyl;
R$^{3a}$ is —H or —C$_{1-3}$alkyl optionally substituted with —OCH₃ or 1 to 3 of —F;
each R⁴ is independently —H, halo, or —C$_{1-4}$alkyl optionally substituted with OH or 1-3 of —F;
R⁵ is —H, halo, or —C$_{1-3}$alkyl optionally substituted with —O—C$_{1-3}$alkyl;
R⁶ is —H or —C$_{1-3}$alkyl;
R⁷ is —H or —C$_{1-3}$alkyl, or R⁷ is absent when n is zero;
R⁸ is —H, or R⁸ is absent when n is zero;
R⁹ is —H, —F, —OH, —C$_{1-3}$alkyl, —OC$_{1-3}$alkyl or —CH₂OH;
R¹⁰ is —H, or —C$_{1-3}$alkyl;
R¹¹ is —H, or —C$_{1-3}$alkyl;
R¹², R¹³ and R¹⁴ are each independently —H, halo, —CN, —C$_{3-6}$cycloalkyl, —C(O)OC$_{1-4}$alkyl, —OC$_{1-4}$alkyl, or —C$_{1-4}$alkyl optionally substituted with —OH or 1-3 of —F; and
n is zero or one;
or a pharmaceutically acceptable salt thereof.

4. The compound of claim 1 wherein:
R¹ is —H or halo;
R² is —H;
R$^{3a}$ is —H or —C$_{1-3}$alkyl;
each R⁴ is —H;
R⁵ is —H, halo, or —C$_{1-3}$alkyl;
R⁶ is —H or —C$_{1-3}$alkyl;
R⁷ is —H, or R⁷ is absent when n is zero;
R⁸ is —H, or R⁸ is absent when n is zero;
R⁹ is —H, —F, —OH, —C$_{1-3}$alkyl, —OC$_{1-3}$alkyl or —CH₂OH;
R¹⁰ is —H;
R¹¹ is —H;
R¹², R¹³ and R¹⁴ are each independently —H, halo, —OC$_{1-4}$alkyl, or —C$_{1-4}$alkyl optionally substituted with —OH or 1-3 of —F; and
n is zero or one;
or a pharmaceutically acceptable salt thereof.

5. The compound of claim 1 wherein R⁹ is —OH; or a pharmaceutically acceptable salt thereof.

6. The compound of claim 1 wherein n is one; or a pharmaceutically acceptable salt thereof.

7. A compound which is:
8-(2-(4-(2H-tetrazol-2-yl)phenyl)-2-hydroxyethyl)-2-(4-methyl-5-oxo-2,5-dihydrofuran-3-yl)-2,8-diazaspiro[4.5]decan-1-one;
8-(2-(4-(4H-1,2,4-triazol-4-yl)phenyl)-2-hydroxyethyl)-2-(4-methyl-5-oxo-2,5-dihydrofuran-3-yl)-2,8-diazaspiro[4.5]decan-1-one;
8-(2-(6-(4H-1,2,4-triazol-4-yl)pyridin-3-yl)-2-hydroxyethyl)-2-(4-methyl-5-oxo-2,5-dihydrofuran-3-yl)-2,8-diazaspiro[4.5]decan-1-one;
(S)-8-(2-(4-(2H-tetrazol-2-yl)phenyl)-2-hydroxyethyl)-2-(4-methyl-5-oxo-2,5-dihydrofuran-3-yl)-2,8-diazaspiro[4.5]decan-1-one;
(S)-8-((S)-2-(4-(2H-tetrazol-2-yl)phenyl)-2-hydroxyethyl)-3-methyl-2-(5-oxo-2,5-dihydrofuran-3-yl)-2,8-diazaspiro[4.5]decan-1-one;
(S)-8-((R)-2-(4-(2H-tetrazol-2-yl)phenyl)-2-hydroxyethyl)-3-methyl-2-(5-oxo-2,5-dihydrofuran-3-yl)-2,8-diazaspiro[4.5]decan-1-one;
or a pharmaceutically acceptable salt thereof.

8. A pharmaceutical composition comprising a compound of claim 1 or a pharmaceutically acceptable salt thereof and a pharmaceutically acceptable carrier.

9. The pharmaceutical composition of claim 8 further comprising an additional active agent selected from losartan, valsartan, candesartan, olmesartan, telmesartan, eprosartan, irbesartan, amlodipine, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril, amiloride, spironolactone, epleranone or triamterene, or a pro-drug thereof, or a pharmaceutically acceptable salt of any of the foregoing.

10. A method for inhibiting ROMK comprising administering a compound of claim 1 or a pharmaceutically acceptable salt thereof in a ROMK-inhibitory effective amount to a patient in need thereof.

11. A method for the treatment of hypertension comprising administering a compound of claim 1 or a pharmaceutically acceptable salt thereof in a therapeutically effective amount to a patient in need thereof.

* * * * *